United States Patent [19]

Yamashita et al.

[11] Patent Number: 4,479,942
[45] Date of Patent: Oct. 30, 1984

[54] TETRAHYDROFURNANCARBOXYLIC ACID DERIVATIVES, PROCESSES FOR PREPARATION THEREOF AND PHARMACEUTICAL COMPOSITIONS THEREOF

[75] Inventors: Michio Yamashita, Takarazuka; Tadaaki Komori, Takatsuki; Junji Hosoda, Kobe; Yoshio Kawai, Ikeda; Itsuo Uchida, Kyoto; Masanobu Kohsaka, Sakai; Hiroshi Imanaka, Osaka; Kazuo Sakane, Amagasaki; Hiroyuki Setoi, Toyonaka; Tsutomu Teraji, Osaka, all of Japan

[73] Assignee: Fujisawa Pharmaceutical Co., Ltd., Osaka, Japan

[21] Appl. No.: 403,117

[22] Filed: Jul. 29, 1982

[30] Foreign Application Priority Data

Aug. 10, 1981 [GB] United Kingdom ............... 8124352

[51] Int. Cl.³ .................... A61K 31/70; C07H 17/00; C07H 19/06
[52] U.S. Cl. ..................... 424/180; 536/24; 536/26
[58] Field of Search ............ 536/24, 26; 424/180; 544/277

[56] References Cited

U.S. PATENT DOCUMENTS

| | | |
|---|---|---|
| 2,852,506 | 9/1958 | Goldman et al. ............ 544/277 |
| 2,985,564 | 5/1961 | Weindling ................. 195/80 |
| 3,825,541 | 7/1974 | Vince ..................... 544/277 |
| 3,868,451 | 2/1975 | Stein et al. ............... 424/180 |
| 4,205,164 | 5/1980 | Kirst ..................... 536/26 X |
| 4,224,438 | 9/1980 | Fauland et al. ............ 536/24 |

FOREIGN PATENT DOCUMENTS 2034785 1/1972 Fed. Rep. of Germany ...... 544/277

OTHER PUBLICATIONS

Fraser et al., Proc. Natl. Acad. Sci. USA vol. 70, No. 9, pp. 2671-2675 (Sep. 1973).
Chemical Abstracts 96:p2159q (1981).

Primary Examiner—Ethel G. Love
Attorney, Agent, or Firm—Oblon, Fisher, Spivak, McClelland & Maier

[57] ABSTRACT

This invention relates to tetrahydrofuran-carboxylic acid derivatives, of antimicrobial activity, of the formula:

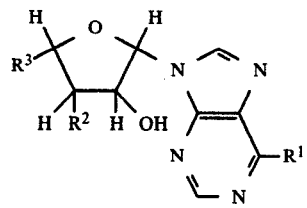

wherein
$R^1$ is amino or a protected amino group,
$R^2$ is amino or acylamino and
$R^3$ is carboxy or a protected carboxy group
or a pharmaceutically acceptable salt thereof.

11 Claims, No Drawings

TETRAHYDROFURANCARBOXYLIC ACID DERIVATIVES, PROCESSES FOR PREPARATION THEREOF AND PHARMACEUTICAL COMPOSITIONS THEREOF

This invention relates to tetrahydrofurancarboxylic acid derivatives. More particularly, this invention relates to tetrahydrofurancarboxylic acid derivatives and the pharmaceutically acceptable salts thereof, which have antimicrobial activity, to processes for preparation thereof, and to pharmaceutical compositions comprising the same.

The object tetrahydrofurancarboxylic acid derivatives are novel and can be represented by the following formula:

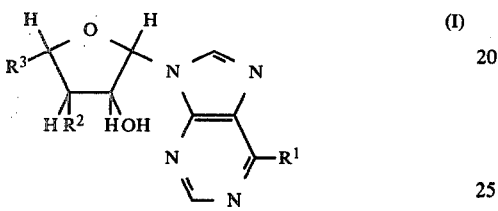

wherein
$R^1$ is amino or a protected amino group,
$R^2$ is amino or acylamino,
$R^3$ is carboxy or a protected carboxy group,
and pharmaceutically acceptable salts thereof.

In the object tetrahydrofurancarboxylic acid derivatives (I) and the corresponding starting compounds mentioned below, it is to be understood that there may be one or more stereoisomeric pair(s) such as optical and geometrical isomers due to asymmetric carbon atom and double bond in those molecules and such isomers are also included within the scope of the present invention, and among the object compound (I), ribofuranuronic acid derivatives are preferable.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

According to the present invention, the object compounds (I) and the pharmaceutically acceptable salts thereof can be prepared by the processes as illustrated by the following reaction schemes.

(A) Synthesis (1) Process 1:

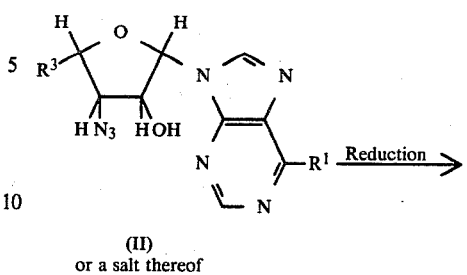

(II)
or a salt thereof

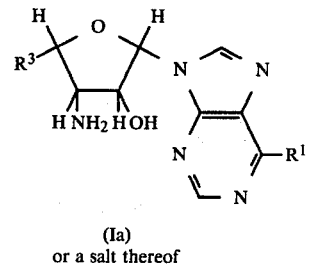

(Ia)
or a salt thereof (2) Process 2:

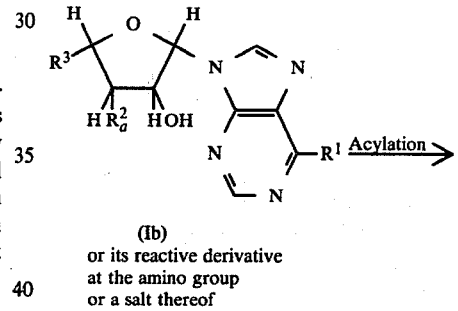

(Ib)
or its reactive derivative
at the amino group
or a salt thereof

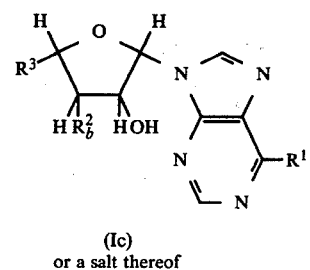

(Ic)
or a salt thereof (3) Process 3:

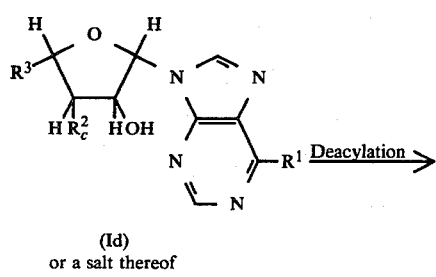

(Id)
or a salt thereof

-continued
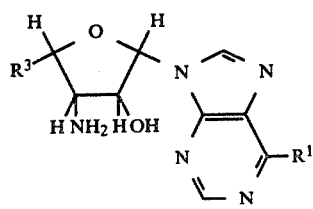
(Ia)
or a salt thereof
(4) Process 4:
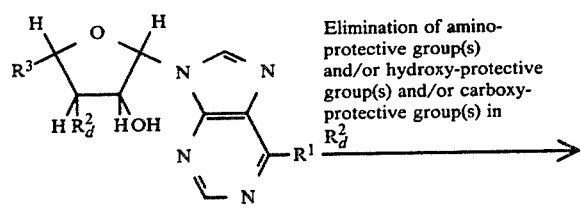
(Ie)
or a salt thereof
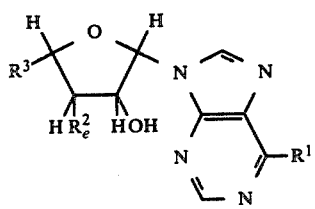
(If)
or a salt thereof
(5) Process 5:
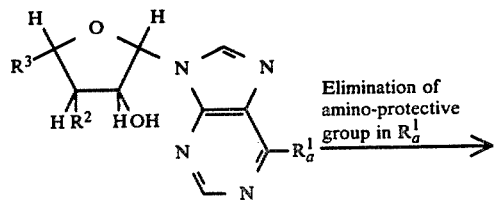
(Ig)
or a salt thereof
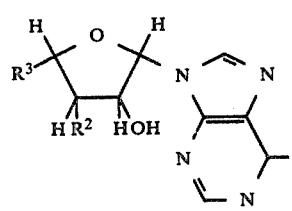
(Ih)
or a salt thereof
(6) Process 6:
-continued
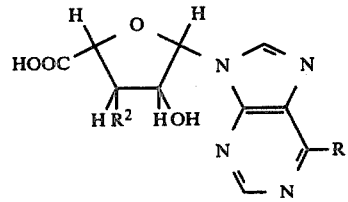
(Ii)
or its reactive derivative
at the carboxy group
or a salt thereof
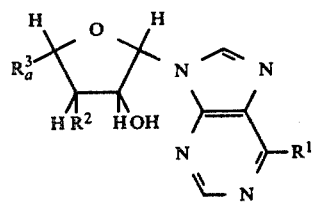
(Ij)
or a salt thereof
(7) Process 7:
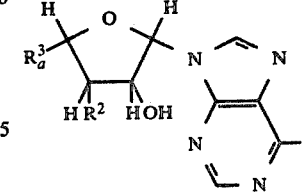
(Ij)
or a salt thereof
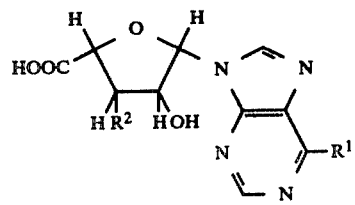
(Ii)
or a salt thereof
(8) Process 8:
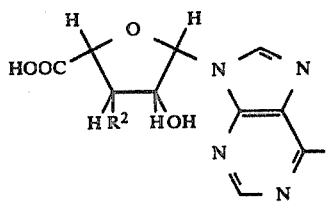
(Ii)
or its reactive derivative
at the carboxy group
or a salt thereof -continued

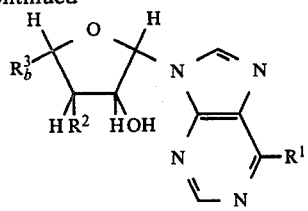

(Ik)
or a salt thereof (9) Process 9:

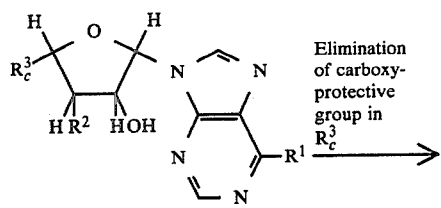

(II)
or a salt thereof

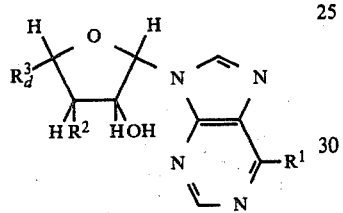

(Im)
or a salt thereof wherein
R[1], R[2] and R[3] are each as defined above,
$R_a^1$ is a protected amino group,
$R_a^2$ is amino or acylamino having an amino group,
$R_b^2$ is acylamino or acylamino having an acylamino group,
$R_c^2$ is acylamino,
$R_d^2$ is acylamino having at least one substituent(s) selected from the groups consisting of protected amino group, protected hydroxy group and protected carboxy group,
$R_e^2$ is acylamino having at least one substituent(s) selected from the groups consisting of amino, hydroxy and carboxy,
$R_a^3$ is an esterified carboxy group,
$R_b^3$ is an amidated carboxy group,
$R_c^3$ is an amidated carboxy group having a protected carboxy group, and
$R_d^3$ is an amidated carboxy group having a carboxy group.

(B) Fermentation

Among the object compound (I), 1-(6-amino-9H-purin-9-yl)-1,3-dideoxy-3-(O-methyl-L-tyrosylamino)-β-D-ribofuranuronic acid (hereinafter referred to FR-48736 substance) or a salt thereof may be prepared by fermentation using a strain belonging to the genus Chrysosporium.

Starting compound (II) used in Process 1 are new and can be prepared, for example, from the known compound by the method in the following preparations or in a similar manner thereto.

Preparation 1:

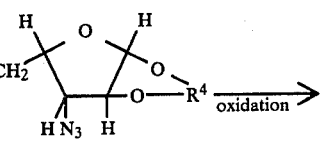

(IIIa)

oxidation →

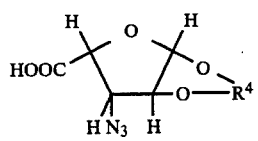

(IIIb)
or a salt thereof

Preparation 2:

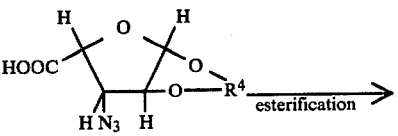

(IIIb)
or a salt thereof esterification →

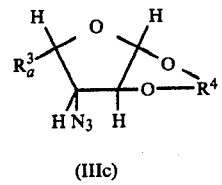

(IIIc)

Preparation 3:

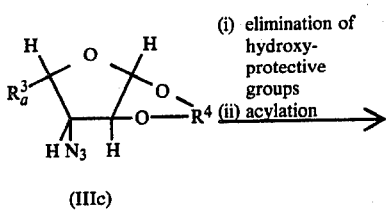

(IIIc)

(i) elimination of hydroxy-protective groups
(ii) acylation →

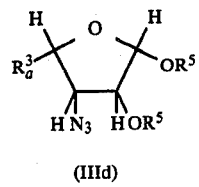

(IIId)

Preparation 4:

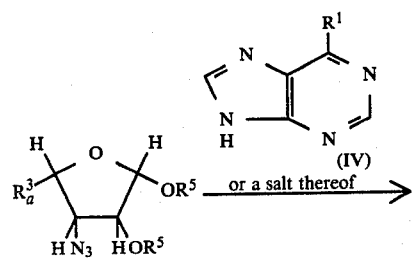

(IIId)

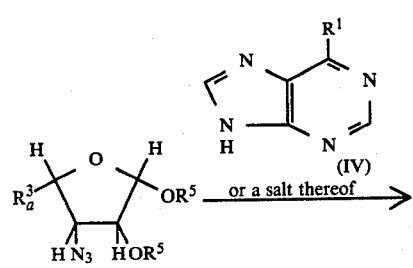

(IV)
or a salt thereof →

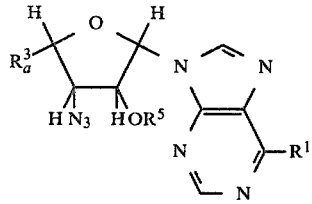

(IIa)
or a salt thereof

Preparation 5:

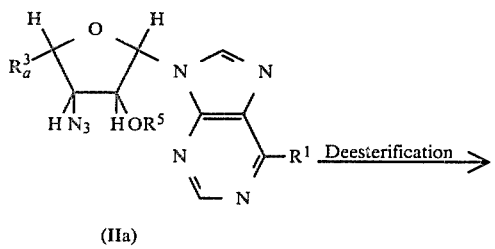

(IIa)
or a salt thereof

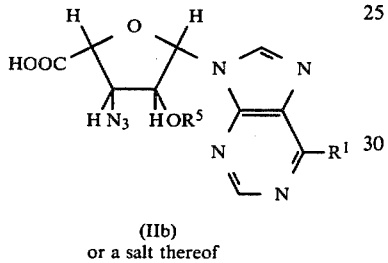

(IIb)
or a salt thereof

Preparation 6:

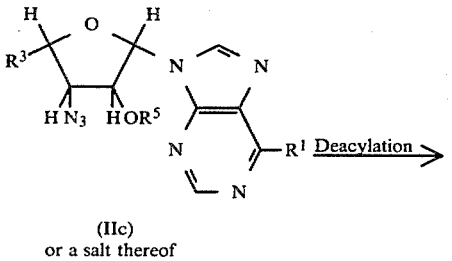

(IIc)
or a salt thereof

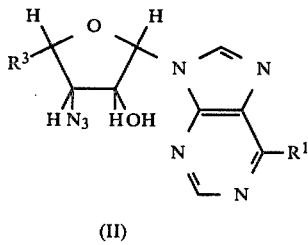

(II)
or a salt thereof wherein
$R^1$, $R^3$ and $R_a^3$ are each as defined above,
$R^4$ is lower alkylidene and
$R^5$ is acyl.

Suitable salt of the object compounds (Ia)–(Im) and the starting compounds (II), (IIa)–(IIc), (IIIb) and (IV) may be referred to the same ones as illustrated for the compound (I).

In the subsequent description of the present specification, suitable examples and illustration of the various definitions to be included within the scope thereof are explained in detail as follows.

The term "lower" in the present specification is intended to mean a group having 1 to 6 carbon atom(s), unless otherwise indicated.

Suitable "protected amino" group may include an amino group substituted by a conventional amino-protective group, for example, acyl as mentioned below, ar(lower)alkyl such as mono-(or di or tri)phenyl(lower-)alkyl (e.g. benzyl, benzhydryl, trityl, etc.), lower alkoxycarbonyl(lower)alkylidene or its enamine tautomer (e.g. 1-methoxycarbonyl-1-proten-2-yl, etc.), di(lower-)alkylaminomethylene (e.g. dimethylaminomethylene, etc.), etc.

Suitable "acyl" or "acyl moiety" in the term of "acylamino" may include an aliphatic acyl, an aromatic acyl, and an aliphatic acyl substituted with aromatic group(s).

The aliphatic acyl may include saturated or unsaturated ones, such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), and the like.

The aromatic acyl may include aroyl (e.g. benzoyl, toluoyl, xyloyl, etc.), and the like.

The aliphatic acyl substituted with aromatic group(s) may include ar(lower)alkanoyl such as phenyl(lower)alkanoyl (e.g. phenylacetyl, phenylpropionyl, phenylbutyryl, phenylisobutyryl, phenylvaleryl, phenylisovaleryl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), phenyl(lower)alkenoyl (e.g. cinnamoyl, etc.) and the like.

These acyl groups may be further substituted with one or more substituent(s) such as amino, protected amino group as aforementioned, carboxy, protected carboxy group as illustrated below, guanidino, protected guanidino, for example, 1,3-bis[phenyl(lower)alkoxycarbonyl]guanidino (e.g. 1,3-dibenzyloxycarbonylguanidino, etc.), hydroxy, protected hydroxy group as illustrated below, lower alkoxy (e.g. methoxy, ethoxy, propoxy, isopropoxy, butoxy, etc.), halogen (e.g. fluorine, chlorine, bromine, etc.), nitro, amino(lower)alkoxy (e.g. aminomethoxy, aminoethoxy, aminopropoxy, aminobutoxy, etc.), protected amino(lower)alkoxy group, for example, lower alkoxycarbonylamino(lower-)alkoxy (e.g. tert-butoxycarbonylaminomethoxy, tert-butoxycarbonylaminoethoxy, tert-butoxycarbonylaminopropoxy, tert-butoxycarbonylaminobutoxy, etc.), carbazoylamino, lower alkylcarbamoylamino (e.g. methylcarbamoylamino, ethylcarbamoylamino, propylcarbamoylamino, isopropylcarbamoylamino, butylcarbamoylamino, isobutylcarbamoylamino,etc.), carboxy(lower)alkoxy (e.g. carboxymethoxy, carboxyethoxy, carboxypropoxy, etc.), protected carboxy(lower)alkyl group (wherein the protected carboxy moiety is as illustrated below), lower alkanoylamino (e.g. formylamino, acetylamino, etc.) and acylamino as aforementioned (e.g. glycylamino, phenylglycylamino, alanylamino, β-phenylalanylamino, O-methyltyrosylamino, arginylamino, N-benzyloxycarbonylglycylamino, N-tert-butoxycarbonylglycylamino, N-benzyloxycarbonylalanylamino, N-tert-butoxycarbonylalanylamino, N-benzyloxycarbonyl-β-phenylalanylamino, N-tert-butoxycarbonyl-β-phenylalanylamino, N-benzyloxycarbonyl-O-methyltyrosylamino, N-tert-butoxycarbonyl-O-methyltyrosylamino, N-tribenzyloxycarbonylarginylamino, etc.).

Suitable "protected hydroxy group" may include phenyl(lower)alkoxy which may have halogen atoms (e.g. benzyloxy, 4-chlorobenzyloxy, 2,6-dichlorobenzyloxy, etc.) and the like.

Preferred embodiment of "acylamino" for $R^2$ may include lower alkanoylamino having one to two amino group(s) (e.g. glycylamino, alanylamino, β-alanylamino, norvalylamino, valylamino, leucylamino, isoleucylamino, norleucylamino, ornithylamino, lysylamino, etc.);

lower alkanoylamino having one to two of lower alkoxycarbonylamino and/or phenyl(lower)alkoxycarbonylamino group(s) (e.g. N-benzyloxycarbonylglycylamino, N-tert-butoxycarbonylglycylamino, N-benzyloxycarbonylalanylamino, N-tert-butoxycarbonylalanylamino, N-benzyloxycarbonyl-β-alanylamino, N-tert-butoxycarbonyl-β-alanylamino, N-benzyloxycarbonylnorvalylamino, N-tert-butoxycarbonylnorbalylamino, N-benzyloxycarbonylvalylamino, N-tert-butoxycarbonylvalylamino, N-benzyloxycarbonylleucylamino, N-tert-butoxycarbonylleucylamino, N-benzyloxycarbonylisoleucylamino, N-tert-butoxycarbonyl isoleucylamino, N-benzyloxycarbonylnorleucylamino, N-tert-butoxycarbonylnorleucylamino, $N^\alpha,N^\delta$-dibenzyloxycarbonylornithylamino, $N^\alpha,N^\delta$-di-tert-butoxycarbonylornithylamino, $N^\alpha,N^\epsilon$-dibenzyloxycarbonyllysylamino, $N^\alpha,N^\epsilon$-di-tert-butoxycarbonyllysylamino, etc.), lower alkanoylamino having an amino group and a carboxy group (e.g. α-glutamylamino, γ-glutamylamino, etc.), lower alkanoylamino having an amino group and a lower alkoxycarbonyl[or phenyl(lower)alkoxycarbonyl] group (e.g. 2-amino-4-benzyloxycarbonylbutyrylamino, 2-amino-4-tert-butoxycarbonylbutyrylamino, 4-amino-4-benzyloxycarbonylamino, 4-amino-4-tert-butoxycarbonylbutyrylamino, etc.);

lower alkanoylamino having a lower alkoxycarbonylamino[or phenyl(lower)alkoxycarbonylamino] group and a lower alkoxycarbonyl[or phenyl(lower)alkoxycarbonyl] group (e.g. 2-benzyloxycarbonylamino-4-benzyloxycarbonylbutyrylamino, 2-tert-butoxycarbonylamino-4-benzyloxycarbonylbutyrylamino, 4-benzyloxycarbonylamino-4-benzyloxycarbonylbutyrylamino, 4-tert-butoxycarbonylamino-4-benzyloxycarbonylbutyrylamino, etc.);

lower alkanoylamino having an amino group and a guanidino group (e.g. arginylamino, etc.);

lower alkanoylamino having a phenyl(lower)alkoxycarbonylamino group and a bis[phenyl(lower)alkoxycarbonyl]guanidino group (e.g. tribenzyloxycarbonylarginylamino, etc.);

aroylamino (e.g. benzoylamino, etc.);

phenyl(lower)alkanoylamino (e.g. phenylacetylamino, 3-phenylpropionylamino, etc.);

phenyl(lower)alkanoylamino having a hydroxy group (e.g. mandelylamino, etc.);

phenyl(lower)alkanoylamino having one to two amino group(s) (e.g. phenylglycylamino, phenylalanylamino, 3-amino-3-phenylpropionylamino, 2-aminophenylglycylamino, 3-aminophenylglycylamino, 4-aminophenylglycylamino, β-(2-aminophenyl)alanylamino, β-(3-aminophenyl)alanylamino, β-(4-aminophenyl)alanylamino, etc.);

phenyl(lower)alkanoylamino having one to two of lower alkoxycarbonylamino and/or phenyl(lower)alkoxycarbonylamino group(s) (e.g. N-benzyloxycarbonylphenylglycylamino, N-tert-butoxycarbonylphenylglycylamino, N-benzyloxycarbonylphenylalanylamino, N-tert-butoxycarbonylphenylalanylamino, 3-benzyloxycarbonylamino-3-phenylpropionylamino, 3-tert-butoxycarbonyl-3-phenylpropionylamino, N-tert-butoxycarbonyl-2-tert-butoxycarbonylaminophenylglycylamino, N-tert-butoxycarbonyl-3-tert-butoxycarbonylaminophenylglycylamino, N-tert-butoxycarbonyl-4-tert-butoxycarbonylaminophenylglycylamino, N-tert-butoxycarbonyl-β-(2-tert-butoxycarbonylaminophenyl)alanylamino, N-tert-butoxycarbonyl-β-(3-tert-butoxycarbonylaminophenyl)alanylamino, N-tert-butoxycarbonyl-β-(4-tert-butoxycarbonylaminophenyl)alanylamino, etc.);

phenyl(lower)alkanoylamino having a hydroxy group and an amino group (e.g. β-phenylserylamino, tyrosylamino, etc.);

phenyl(lower)alkanoylamino having a hydroxy group and a phenyl(lower)alkoxycarbonylamino group (e.g. N-benzyloxycarbonyl-β-phenylserylamino, etc.);

phenyl(lower)alkanoylamino having a phenyl(lower)alkoxy group and a lower alkoxycarbonylamino[or phenyl(lower)alkoxycarbonylamino] group (e.g. N-benzyloxycarbonyl-O-benzyltyrosylamino, etc.);

phenyl(lower)alkanoylamino having a dihalophenyl(lower)alkoxy group and an amino group [e.g. O-(2,6-dichlorobenzyl)tyrosylamino, etc.];

phenyl(lower)alkanoylamino having a dihalophenyl(lower)alkoxy alkoxy group and a lower alkoxycarbonylamino group (e.g. N-tert-butoxycarbonyl-O-2,6-dichlorobenzyltyrosylamino, etc.);

phenyl(lower)alkanoylamino having an amino group and a lower alkoxy group (e.g. O-methyl-β-phenylserylamino, O-methyltyrosylamino, etc.);

phenyl(lower)alkanoylamino having a lower alkoxycarbonylamino[or phenyl(lower)alkoxycarbonylamino] group and a lower alkoxy group (e.g. N-benzyloxycarbonyl-O-methyl-β-phenylserylamino, N-tert-butoxycarbonyl-O-methyl-β-phenylserylamino, N-benzyloxycarbonyl-O-methyltyrosylamino, N-tert-butoxycarbonyl-O-methyltyrosylamino, etc.);

phenyl(lower)alkanoylamino having an amino group and a halogen atom [e.g. β-(2-chlorophenyl)alanylamino, β-(3-chlorophenyl)alanylamino, β-(4-chlorophenyl)-alanylamino, β-(4-fluorophenyl)alanylamino, etc.];

phenyl(lower)alkanoylamino having a lower alkoxycarbonylamino[or phenyl(lower)alkoxycarbonylamino] group and a halogen atom [e.g. N-benzyloxycarbonyl-β-(2-chlorophenyl)alanylamino, N-tert-butoxycarbonyl-β-(2-chlorophenyl)alanylamino, N-benzyloxycarbonyl-β-(3-chlorophenyl)alanylamino, N-tert-butoxycarbonyl-β-(3-chlorophenyl)alanylamino, N-benzyloxycarbonyl-β-(4-chlorophenyl)alanylamino, N-tert-butoxycarbonyl-β-(4-chlorophenyl)alanylamino, N-benzyloxycarbonyl-β-(4-fluorophenyl)alanylamino, N-tert-butoxycarbonyl-β-(4-fluorophenyl)alanylamino, etc.];

phenyl(lower)alkanoylamino having an amino group and a nitro group [e.g. β-(4-nitrophenyl)alanylamino, etc.];

phenyl(lower)alkanoylamino having a lower alkoxycarbonylamino[or phenyl(lower)alkoxycarbonylamino] group and a nitro group [e.g. N-benzyloxycarbonyl-β-(4-nitrophenyl)alanylamino, N-tert-butoxycarbonyl-β-(4-nitrophenyl)alanylamino, etc.];

phenyl(lower)alkanoylamino having an amino group and an amino(lower)alkoxy group [e.g. O-(3-aminopropyl)tyrosylamino, etc.];

phenyl(lower)alkanoylamino having a lower alkoxycarbonylamino group and a lower alkoxycarbonylamino(lower)alkoxy group [e.g. N-tert-butoxycarbonyl-O-(3-tert-butoxycarbonylaminopropyl)-tyrosylamino, etc.];

phenyl(lower)alkanoylamino having a lower alkoxy group and a carbazoylamino group (e.g. N-carbazoyl-O-methyltyrosylamino, etc.);

phenyl(lower)alkanoylamino having a lower alkoxy and a lower alkylcarbamoylamino group (e.g. N-butylcarbamoyl-O-methyltyrosylamino, etc.);

phenyl(lower)alkanoylamino having an amino group and a carboxy(lower)alkoxy group (e.g. O-carboxymethyltyrosylamino, etc.);

phenyl(lower)alkanoylamino having a lower alkoxycarbonylamino group and a lower alkoxycarbonyl(lower)alkoxy group (e.g. N-tert-butoxycarbonyl-O-methoxycarbonylmethyltyrosylamino, etc.);

phenyl(lower)alkanoylamino having a lower alkanoylamino group (e.g. N-formylphenylalanylamino, etc.);

phenyl(lower)alkanoylamino having a nitrophenyl(lower)alkoxycarbonyl group [e.g. 2-(4-nitrobenzyloxycarbonyl-2-phenylacetylamino, etc.];

phenyl(lower)alkanoylamino having a lower alkoxy group and an amino(lower)alkanoylamino group [e.g. N-glycyl-O-methyltyrosylamino, etc.];

phenyl(lower)alkanoylamino having a lower alkoxy group and a phenyl(lower)alkoxycarbonylamino(-lower)alkanoylamino group [e.g. N-(N-benzyloxycarbonylglycyl)-O-methyltyrosylamino, etc.];

phenyl(lower)alkanoylamino having a lower alkoxy group and a phenyl(lower)alkanoylamino having an amino (or lower alkoxycarbonylamino) group [e.g. N-(β-phenylalanyl)-O-methyltyrosylamino, N-(N-tert-butoxycarbonyl-β-phenylalanyl)-O-methyltyrosylamino, etc.];

phenyl(lower)alkanoylamino having a lower alkoxy group and a lower alkoxyphenyl(lower)alkanoylamino having an amino (or lower alkoxycarbonylamino) group [e.g. N-(O-methyltyrosyl)-O-methyltyrosylamino, N-(N-tert-butoxycarbonyl-O-methyltyrosyl-O-methyltyrosylamino, etc.];

phenyl(lower)alkanoylamino having a lower alkoxy group and a guanidino(lower)alkanoylamino having an amino group [e.g. N-arginyl-O-methyltyrosylamino, etc.];

phenyl(lower)alkanoylamino having a lower alkoxy group and a bis[phenyl(lower)alkoxycarbonyl]-guanidino(lower)alkanoylamino having a phenyl(-lower)alkoxycarbonylamino group, [e.g. N-(tribenzyloxycarbonylarginyl)-O-methyltyrosylamino, etc.]; and phenyl(lower)alkenoylamino (e.g. cinnamoylamino, etc.).

Suitable "protected carboxy group" and "protected carboxy moiety" in the term "protected carboxy(lower)alkyl" may include an esterifier carboxy group and an amidated carboxy group.

Suitable ester moiety in said esterified carboxy group may include the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.), which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)halo(lower)alkyl ester (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.); mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-dri-tert-butylbenzyl ester, etc.), heterocyclic ester (e.g. N-hydroxysuccinimide ester, etc.), and the like.

Suitable amidated carboxy group may include carbamoyl, lower alkylcarbamoyl (e.g. methylcarbamoyl, ethylcarbamoyl, propylcarbamoyl, isopropylcarbamoyl, butylcarbamoyl, isobutylcarbamoyl, etc.), carbazoyl, carboxy(lower)alkylcarbamoyl (e.g. carboxymethylcarbamoyl, carboxyethylcarbamoyl, carboxypropylcarbamoyl, carboxybutylcarbamoyl, etc.), carboxy(lower)alkylcarbamoyl having a phenyl group (e.g. α-carboxyphenethylcarbamoyl, etc.) and phenyl(-lower)alkoxycarbonyl(lower)alkylcarbamoyl having a phenyl group (e.g. α-benzyloxycarbonylphenethylcarbamoyl, etc.).

The processes for the preparation of the object compound (I) of the present invention are explained in details in the following.

(A) SYNTHESIS (1) Process 1

The compound (Ia) or a salt thereof can be prepared by reducing the compound (II) or a salt thereof.

The reduction can be carried out by a conventional method such as reduction using a reducing agent, catalytic reduction, or the like.

Suitable reducing agent may include a combination of a metal (e.g. tin, zinc, iron, etc.), or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.), a combination of hydrogen sulfide and a base (e.g. triethylamine, etc.) and the like.

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g.

reduced copper, Raney copper, Ullman copper, etc.) and the like.

This reaction is usually carried out in a solvent such as water, alcohol (e.g. methanol, ethanol, etc.), ethyl acetate, tetrahydrofuran or any other solvent which does not adversely affect the reaction. These solvents may be used as a mixture thereof.

The reaction temperature is not critical and the reaction is usually carried out under cooling to heating.

(2) Process 2

The compound (Ic) or a salt thereof can be prepared by reacting the compound (Ib) or its reactive derivative at the amino group or a salt thereof with an acylating agent. The acylating agent can be shown by the formula: $R^5$—OH (V) (wherein $R^5$ is acyl) or its reactive derivative or a salt thereof.

Suitable reactive derivative at the amino group of the compound (Ib) may include a conventional one, for example, a silyl derivative formed by the reaction of the compound (Ib) with a silyl compound such as (trimethylsilyl)acetamide or trimethylsilylacetamide, and the like.

Suitable reactive derivative of the compound (V) may include, for example, an acid halide, an acid anhydride, an activated ester, an acid azide, and the like, and preferably an ester with a N-hydroxy compound such as N-hydroxysuccinimide, N-hydroxyphthalimide, 1-hydroxybenzotriazole, 1-hydroxy-6-chlorobenzotriazole, etc.), and the like.

The suitable reactive derivatives of the compound (Ib) or (V) can optionally be selected from the above according to the kinds of the compounds (Ib) or (V) to be used practically.

This reaction can be carried out in the presence of an organic or inorganic base such as alkali metal (e.g. lithium, sodium, potassium etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

In case that the compound (V) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], N-ethoxycarbonyl-2-ethoxy-1,2-dihydroquinoline; a ketenimine compound (e.g. pentamethyleneketene-N-cyclohexylimine, diphenylketene-N-cyclohexylimine, etc.), N,N-carbonylbis(2-methylimidazole; an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.) N-methylformamide or the like with a halogen compound such as thionyl chloride, phosphoryl chloride, phosgene or the like.

In the present reaction, the compound (Ic) wherein $R_b^2$ is mandelylamino can also be obtained by using 2,4-dioxo-5-phenyl-1,3-dioxolane as a reactive derivative of mandelic acid.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to heating.

(3) Process 3

The object compound (Ia) or a salt thereof can be prepared by subjecting the compound (Id) or a salt thereof to deacylation reaction. The present reaction can preferably carried out by hydrolysis in the presence of a base.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene,anion-exchange resin or the like.

Suitable solvent includes water, alcohol (e.g. methanol, ethanol, etc.), tetrahydrofuran or any other organic solvents which do not adversely influence the reaction, or a mixture thereof.

The reaction temperature is not critical and may suitably be selected in accordance with the kind of the acyl group, and the reaction is usually carried out under warming to heating.

(4) Process 4

The compound (If) or a salt thereof can be prepared by subjecting the compound (Ie) or a salt thereof to elimination reaction of the aminoprotective group(s) and/or the hydroxy-protective groups(s) and/or the carboxy-protective group(s) in $R_d^2$.

Suitable method for this removal reaction may include conventional one such as hydrolysis, reduction, and the like.

Hydrolysis is preferably carried out in the presence of an acid or a base.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. Suitable base may be an inorganic base (e.g. sodium hydroxide, potassium hydroxide, ammonium hydroxide, etc.), an organic base (e.g. trimethyl amine, butyl amine, etc.), and the like. In case that the organic acid such as trifluoroacetic acid and p-toluenesulfonic acid is used in this reaction, the reaction is preferably carried out in the presence of cation trapping agents (e.g. anisole, etc.).

The acid or the base suitable for this hydrolysis can be selected according to the kinds of the protective group to be removed. The acid hydrolysis can preferably be applied to the amino-protective group.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to heating.

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed.

For example, the reduction can preferably be applied to the amino-protective group and the catalytic reduction can preferably be applied to the carboxy- or hydroxy-protective group.

The reduction is usually carried out in a conventional solvent which does not adversely influence the reaction such as water, methanol, ethanol, propanol, N,N-dimethylformamide, or a mixture thereof.

Additionally, in case that the above-mentioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

(5) Process 5

The compound (Ih) or a salt thereof can be prepared by subjecting the compound (Ig) or a salt thereof to elimination reaction of the amino-protective group in $R_a^1$.

This reaction can be conducted by a similar manner to that of Process 4.

Further, the present reaction can also be carried out by using a lower alkyl amine (e.g. propylamine, butylamine, etc.), preferably in the presence of a solvent such as alcohol (e.g. water, methanol, ethanol, propanol, isopropanol, butanol, etc.) under cooling to heating.

(6) Process 6

The compound (Ij) or a salt thereof can be prepared by subjecting the compound (Ii) or its reactive derivative at the carboxy group or a salt thereof, to esterification reaction. Suitable reactive derivative at the carboxy group of the compound (Ii) may be referred to that of the compound (V) illustrated in the Process 2.

This esterification can be conducted by reacting the compound (Ii) or its reactive derivative at the carboxy group or a salt thereof with a conventional esterifying agent such as an alcohol or its reactive equivalent (e.g. halide, sulfonate, sulfate, diazo compound, etc.) and the like.

The reaction can also be carried out in the presence of a base, and suitable examples thereof are the same as those given in the explanation of Process 2.

This reaction is usually carried out in a conventional solvent which does not adversely influence the reaction such as N,N-dimethylformamide, tetrahydrofuran, dioxane, methanol, ethanol, etc., or a mixture thereof.

The reaction temperature is not critical, and the reaction is usually carried out under cooling to heating.

In case that the alcohol per se is used as the esterifying agent, the reaction can also be carried out in the presence of a condensing agent as illustrated in Process 2.

(7) Process 7

The compound (Ii) or a salt thereof can be prepared by subjecting the compound (Ij) or a salt thereof to deesterification reaction of the esterified carboxy group for $R_a^3$.

This reaction is carried out by a conventional method such as hydrolysis, reduction, and the like.

Hydrolysis can be preferably carried out in the presence of a base, and the suitable example thereof are the same as those given in the explanation of Process 2, and the reaction is usually carried out in a solvent such as water, alcohol (e.g. methanol, ethanol, etc.), tetrahydrofuran or any other solvent which does not adversely affect the reaction. These solvent may be used as a mixture thereof. The reaction temperature is not critical and the reaction is usually carried out under cooling to heating.

(8) Process 8

The object compound (Ik) or a salt thereof can be prepared by subjecting the compound (Ii) or its reactive derivative at the carboxy group or a salt thereof to amidation reaction.

This amidation can be carried out by reacting the compound (Ii) or its reactive derivative at the carboxy group or a salt thereof with an amino-compound of the formula: $R^6$—$NH_2$ (VI) [wherein $R^6$ is hydrogen, amino or an organic group such as lower alkyl which may have a carboxy group, phenyl(lower)alkyl which may have a protected carboxy group or the like.] or its reactive derivative at the amino group or a salt thereof.

Suitable reactive derivative at the carboxy group of the compound (Ii) and suitable reactive derivative at the amino group of the compound (VI) may be referred to those of the compound (V) and the compound (Ib) illustrated in Process 2, respectively.

This reaction can be carried out in a similar manner to that of Process 2.

(9) Process 9

The compound (Im) or a salt thereof can be prepared by subjecting the compound (Il) or a salt thereof to elimination reaction of the carboxy-protective group in $R_c{}^3$.

The present elimination reaction can be carried out in a similar manner to that of Process 4.

In the above Process 1 to 9, in case that the compounds (Ia), (Ic), (If), (Ih), (Ij), (Ii), (Ik) and (Im) have free carboxy and/or free amino group(s), it may be transformed into its salts by a conventional method.

(B) FERMENTATION

The FR-48736 substance or its pharmaceutically acceptable salts of this invention can be produced by fermentation of a FR-48736 substance producing strain belonging to the genus Chrysosporium such as *Chrysosporium pannorum*, more specifically *Chrysosporium pannorum* (Link) Hughes No. 4629, or the like in a nutrient medium.

(1) Microorganism

The microorganisms which can be used for the production of FR-48736 substance or its pharmaceutically acceptable salts are strains belonging to the genus Chrysosporium, among which a strain of *Chrysosporium pannorum* (Link) Hughes No. 4629 has been newly isolated from a soil sample collected at Otaru city, Hokkaido Prefecture in Japan as a suitable strain of FR-48736 substance-producing strain belonging to the genus Chrysosporium.

A culture of the newly isolated living organism of *Chrysosporium pannorum* (Link) Hughes No. 4629 is deposited with the American Type Culture Collection, 12301 Parklawn Drive, Rockville, Md. 20852 USA, under the ATCC Accession Number 20617 (depositing date: July 16, 1981) and is hereinafter designated as *Chrysosporium pannorum* (Link) Hughes No. 4629 ATCC 20617. It is to be understood that, for the production of the FR-48736 substance, this invention is not limited to the use of the particular organism as described herein, which is given for illustrative purpose only. This invention also includes the use of any mutants which are capable of producing the FR-48736 substance, including natural mutants of the organisms as well as artificial mutants which can be produced from the described organism by conventional means including genetic engineering.

*Chrysosporium pannorum* (Link) Hughes No. 4629 ATCC 20617 has the following morphological and cultural characteristics:

(i) Marphological Characteristics:

The microscopic observations show the following morphological properties.

The semi-macronematous conidiophores are erect, short or tall, up to 30μ long and 1–2μ wide, septated and straight. They are simple or verticillately branched at nearly right to acute angles, and secondary, tertiary or more higher laterals may be produced from the branches.

A main axis of the conidiophore is rarely sterile. The fertile laterals produce the unicellular, hyaline conidia at the tips or in an intercalary position, and rarely along the sides.

The strain No. 4629 has two-type conidia, aleuriospores and arthrospores. Aleuriospores, formed at the apex of conidiophores, are pyriform or subglobose, roughened, 3–4.5μ×2.5–4μ in size and 1–1.5μ wide at the truncated base. Arthrospores, borne in the intercalary position of conidiophores and vegetative hyphae, are oblong or lenticular, smooth or roughened, 4–6μ×1.5–2.5μ on size and 1–1.5μ wide at the both truncate ends with abroad scar.

(ii) Cultural Characteristics

Colonies on malt extract agar grow very restrictedly, attaining 10 mm in diameter after 2 weeks at 25° C., and are raised, dense and dry with a furrow-like or crust-like surface. The color on the surface is pale yellow orange to pale yellow brown or pale red. The conidial formation is very limited and the reverse is yellow brown. Colonies on Czapek's solution agar are similar to those on malt extract agar in rate of growth, but the surface is plane and felty or powdery and pale yellow orange to pale orange. The reverse is dull red to reddish orange. On corn meal agar the colony size attained 10 mm in diameter. Surface color of colony varies from white to pale green, bluish white, yellow, orange and grey. Frequently the colony is studded with small droplets of pale brown or reddish orange exudation. Conidia are produced in abundance. The reverse is pale yellow orange or pale brown.

The range of growth temperature and optimum temperature were determined on potato dextrose agar using a temperature gradient incubator(Toyo Kagaku Sangyo Co., Ltd.). The strain No. 4629 can grow at temperature in the range of from 1° to 29° C. with the growth optimum at 17° C. Cultures at 5° C. show very slow growth, attaining 6–8 mm in diameter after 2 weeks at 25° C. The surface is plane and funiculose or fasciculate and white to pale yellow orange. Conidia are not formed and the reverse is the same color as the surface. The strain can grow at pH 4–9 and has a growth optimum at pH 5.

After comparing the above-stated characters with Carmichael's description, Canadian Journal of Botany, 40, 1162(1962), the strain No. 4629 is considered to be *Chrysosporium pannorum* (Link) Hughes.

(2) Preparation of FR-48736 substance

FR-48736 substance or its pharmaceutically acceptable salts of this invention is produced when a FR-48736 substance-producing strain belonging to the genus Chrysosporium (e.g. *Chrysosporium pannorum* (Link) Hughes No. 4629 ATCC 20617 is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, glycerin, starch and the like. Other sources which may be included are galactose, maltose, dextrin, and the like.

The preferred sources of nitrogen are yeast extract, peptone, gluten meal, cottonseed meal, soybean meal, peanut meal, corn steep liquor, dried yeast, casein hydrolysate, wheat germ, beast bone extract, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not used in their pure form because less pure materials, which contain traces of growth factors and considerable quantities of mineral nutrients, are also suitable for use. When desired, there may be added to the medium mineral salts such as calcium carbonate, sodium or potassium phosphate, sodium or potassium chloride, magnesium salts, copper salts and the like. If necessary, especially when the culture medium foams seriously a defoaming agent, such as liquid paraffin, fatty oil, plant oil, mineral oil or silicone may be added.

As in the case of the production of other antibiotics in massive amounts, submerged aerobic cultural conditions are preferred for the production of FR-48736 substance in massive amounts. For the production in small amounts, a shaking or surface culture in a flask or bottle is employed. Furthermore, when the growth is carried out in a large scale, it is preferable to use the vegetable broth of the organism for inoculation in the production fermenter (jar-fermenter, tank, etc.) in order to avoid growth lag in the process of production of FR-48736 substance. Accordingly, it is desirable first to produce a vegetative broth of the organism by inoculating a relatively small quantity of culture medium with spores or mycelia of the organism and culturing said inoculated medium, and then to transfer the cultured vegetative broth aseptically to a large fermenter. The medium, in which the vegetative broth is produced, is substantially the same as or different from the medium utilized for the production of FR-48736 substance.

The fermentation is usually conducted at a temperature between about 20° C. and 40° C., preferably 23°-28° C., for a period of about 50 hours to 200 hours.

Thus produced FR-48736 substance can be isolated from the culture medium by conventional means which are commonly used for the isolation of other known antibiotics. In general, most of FR-48736 substance produced are found in the culture broth, and accordingly FR-48736 substance can be separated from the filtrate, which is obtained by filtering or centrifuging the culture broth, by a conventional method such as concentration under reduced pressure, lyophilization, pH adjustment, treatment with a resin (e.g. anion or cation exchange resin, polymeric adsorbent, etc.), treatment with a conventional adsorbent (e.g. activated charcoal, silicic acid, silica gel, cellulose, alumina), crystallization and the like.

FR-48736 substance thus produced in the culture broth can be isolated in the free form, i.e., FR-48736 substance per se or in the form of its pharmaceutically acceptable salts. When the solution containing FR-48736 substance is treated with a base, i.e. with an inorganic base such as an alkali metal compound (e.g. sodium hydroxide, potassium hydroxide, etc.), an alkaline earth metal compound (e.g., calcium hydroxide, magnesium hydroxide, etc.), ammonia and the like, with an organic base (e.g. ethanolamine, triethylamine, dicyclohexylamine, morpholine, etc.); or with an acid i.e. with an inorganic acid (e.g. hydrochloric acid, sulfuric acid, phosphoric acid, etc.); or with an organic acid (e.g. formic acid, acetic acid, lactic acid, p-toluenesulfonic acid, citric acid, tartaric acid, etc.) during operation of the processes, e.g. extraction, isolation or purification processes or process for transforming FR-48736 substance to its pharmaceutically acceptable salt, FR-48736 substance may be transformed into corresponding salts. The corresponding salts can be isolated from the resulting reaction mixture in a conventional manner.

Alternatively, the salts of FR-48736 substance can be converted to the free form, i.e. FR-48736 substance per se in a conventional manner.

(3) Physical and chemical properties of FR-48736 substance

FR-48736 substance or its pharmaceutically acceptable salts possesses the following physical and chemical properties;

(i) FR-48736 substance per se: (monohydrate, prepared in Example 97)
 (a) Form and color: Colorless needles.
 (b) Nature of substance: Amphoteric.
 (c) Melting point: 228°-232° C. (dec.).
 (d) Elementary analysis: C 50.62, H 4.98, N 21.02 (%).
 (e) Infrared absorption spectrum: $\nu$ (max) (Nujol): 3300, 3150, 2050, 1680, 1610, 1575, 1540, 1515, 1440, 1420, 1350, 1340, 1330, 1305, 1295, 1285, 1250(Sh.), 1230, 1215, 1185, 1180(Sh.), 1170, 1155, 1140, 1130, 1110, 1100, 1090, 1070, 1065, 1045, 1030, 1010, 980, 960, 940, 900, 790, 730, 720, 700(Sh.), 690, 680, 660 cm$^{-1}$.

(ii) Hydrochloride of FR-48736 substance: (dihydrate, prepared in Example 98)
 (a) Form and color: Colorless needles.
 (b) Melting points: 198°-220° C. (dec.).
 (c) Elementary analysis: C 45.14, H 5.01, N 18.67, Cl 7.04 (%).

(iii) Dihydrochloride of FR-48736 substance: (monohydrate prepared in Example 98)
 (a) Form and color: Colorless needles.
 (b) Melting point: 215°-233° C. (dec.).
 (c) Elementary analysis: C 43.49, H 4.82, N 18.25, Cl 13.04.
 (d) Infrared absorption spectrum: $\nu$ (max) (Nujol): 3600-2200, 1720 (Sh.), 1695, 1665, 1630, 1610, 1560, 1510, 1470, 1455, 1440, 1410, 1395, (Sh.), 1370, 1360, 1345, 1300, 1250, 1230, 1220, 1175, 1150, 1130, 1110, 1075, 1025, 1005, 955, 940, 905, 855, 825, 815, 780, 740, 715, 665 cm$^{-1}$.
 (e) 1H-Nuclear magnetic resonance absorption spectrum: (DCl-D$_2$O,$\delta$): 3.23 (2H, d, J=8 Hz), 3.84 (3H, s), 4.0 to 4.8 (2H, m), 5.3 to 4.8 (2H, m), 6.25 (1H, d, J=3.0 Hz), 7.03 (2H, d, J=8 Hz), 7.35 (2H, d, J=8 Hz), 8.47 (1H, s), 8.62 (1H, s).
 (f) Specific rotation: $[\alpha]_D^{22}$: +34 (C=1.0, 1N HCl).
 (g) Solubilities to various solvents: Slightly soluble: water and methanol Insoluble: acetone, ethyl acetate and chloroform.
 (h) Color reaction: Positive: iodine reaction, ninhydrin reaction and ceric sulfate reaction Negative: Molisch reaction and ferric chloride reaction.

(i) Ultraviolet absorption spectrum: $\lambda_{max}^{H_2O}$: nm ($E_{1\ cm}^{1\%}$) 260 (715). $\lambda_{max}^{0.1N\ HCl}$: nm($E_{1\ cm}^{1\%}$) 258 (670). $\lambda_{max}^{0.1N\ NaOH}$: nm($E_{1\ cm}^{1\%}$) 260 (730).

(4) Physical and chemical properties of methyl ester of tri or tetra-acetyl FR-48736 substance (i) Preparation:
To a suspension of FR-48736 substance (20 mg) in pyridine (3 ml) was added acetic anhydride (1 ml), and the whole was stirred at ambient temperature for 2 days.

To the cooled reaction mixture was added methanol (10 ml) and the resulting solution was condensed under reduced pressure. To the residue was added water and the mixture was extracted with chloroform (10 ml×3). The combined extract was washed with a 1N-hydrochloric acid solution and brine, and then dried over sodium sulphate. Evaporation of the solvent under reduced pressure gave a residue, which was purified by preparative thin layer chromatography on silica gel (Merck & Co., Inc., layer thickness 0.5 mm; 20×20 cm×1) developed with a mixture of chloroform and methanol (5:1). The bands which contain the object compounds were extracted with a mixture of chloroform and methanol (5:1). The extracts were condensed under reduced pressure and the residues were dried up by using high vacuum pump to afford a methyl ester of tetraacetylated FR-48736 substance (8 mg) and a methyl ester of triacetylated FR-48736 substance (4 mg) as white powder respectively.

(ii) Physical and chemical properties of methyl ester of triacetylated FR-48736 substance:
IR (max)(CHCl$_3$): 1750, 1690, 1660, 1610, 1590, 1510, 1378 cm$^{-1}$ NMR (CDCl$_3$, δ): 8.75 (1H, s), 8.5 (1H, s), 7.16 (2H, d, J=8 Hz), 6.83 (2H, d, J=8 Hz), 6.2 (2H, m), 5.75 (1H, m), 5.1 (1H, m), 4.6 (1H, m), 4.42 (1H, d, J=8 Hz), 3.76 (3H, s), 3.72 (3H, s), 2.96 (2H, d, J=8 Hz), 2.6 (3H, s), 2.15 (3H, s), 1.96 (3H, s).

Mass Spectrum: FD: m/e 597 (M+).

(iii) Physical and chemical properties of methyl ester of tetraacetylated FR-48736 substance;
IR (max)(CHCl$_3$): 1755, 1722, 1660, 1605, 1580, 1515, 1375 cm$^{-1}$ NMR (CDCl$_3$, δ): 8.92 (1H, s), 8.7 (1H, s), 7.15 (2H, d, J=8 Hz), 6.83 (2H, d, J=8 Hz), 6.9 (1H, m), 6.22 (2H, m), 5.76 (1H, m), 5.08 (1H, m), 4.6 (1H, m), 4.42 (1H, d, J=8 Hz), 3.76 (3H, s), 3.72 (3H, s) 2.96 (2H, d, J=8 Hz), 2.36 (6H, s), 2.16 (3H, s), 1.96 (3H, s).

Mass Spectrum: EI: m/e 597 (M+—42). FD: m/e 597 (M+—42).

(5) Physical and chemical properties of hydrolysates of FR-48736 substance (i) Hydrolysis with a base:
Two hydrolysates were prepared by hydrolysation of FR-48736 substance with a base, such as sodium hydroxide, potassium hydroxide and the like.

(a) Preparation:
A solution of hydrochloride dihydrate of FR-48736 substance [1-(6-amino-9H-purin-9-yl)-1,3-dideoxy-3-(O-methyl-L-tyrosylamino)-β-D-ribofuranuronic acid hydrochloride dihydrate] (100 mg) prepared by Example 98 in 1N-methanolic sodium hydroxide (10 ml) was refluxed for 20 hours. To the cooled solution was added water (50 ml) and the methanol in the solution was evaporated under reduced pressure. The resulting aqueous solution was adjusted to pH 7 with 1N-hydrochloric acid and applied to a column of activated charcoal (20 ml). The column was washed with water (40 ml) and eluted with a mixture of methanol and water (1:1) (60 ml). The solvent was evaporated under reduced pressure. The residue was chromatographed on a cellulose column and eluted with a mixture of acetonitrile and water (8:2). The first ninhydrin positive and weak UV absorbing fraction was evaporated under reduced pressure to give a powder of O-methyltyrosine (21 mg).

The second ninhydrin positive and strong UV absorbing fraction was evaporated under reduced pressure to give a powder of 1-(6-amino-9H-purin-9-yl)-1,3-dideoxy-3-amino-β-D-ribofuranuronic acid monohydrate (35 mg).

(b) Physical and chemical properties of O-methyltyrosine:
IR: ν(max) (Nujol): 3400, 3650–2250 (broad), 1675, 1615 cm$^-$.

NMR (DCl-D$_2$O, δ): 7.2 (2H, d, J=8 Hz), 6.93 (2H, d, J=8 Hz), 4.33 (1H, t, J=6 Hz), 3.2 (2H, d, J=6 Hz).

(c) Physical and chemical properties of 1-(6-amino-9H-purin-9-yl)-1,3-dideoxy-3-amino-β-D-ribofuranuronic acid monohydrate):
IR: ν(max) (Nujol): 3480, 3600–2100 (broad), 1655, 1600, 1575 cm$^-$.

NMR (DCl-D$_2$O, δ): 8.43 (1H, s), 8.34 (1H, s), 6.33 (1H, d, J=2 Hz), 5.13 (1H, dd, J=2 Hz, 6 Hz).

FD Mass: 281 (M+1).

$[\alpha]_D^{20}$: −28° (C=0.25, 1N-HCl).

Elementary Analysis: C 39.98, H 4.62, N 28.21, Cl none.

(ii) Hydrolysis with an acid:
(a) Preparation:
A suspension of dihydrochloride monohydrate of FR-48736 substance [1-(6-amino-9H-purin-9-yl)-1,3-dideoxy-3-(O-methyl-L-tyrosylamino)-β-D-ribofuranuronic acid dihydrochloride monohydrate] (300 mg) prepared by Example 98 in 6N hydrochloric acid (20 ml) was refluxed for 12 hours. The resulting solution was cooled and the solvent was evaporated under reduced pressure. The residue was dissolved in water (30 ml) and the solution was adjusted to pH 7 with 1N sodium hydroxide. Then, the solution was applied to a column of Diaion HP 20 (200 ml). The column was washed with water (400 ml) and eluted with a mixture of methanol and water (3:7, 200 ml). The solvent was evaporated under reduced pressure. The residue was chromatographed on a cellulose column and eluted with a mixture of acetonitrile and water (8:2). The fractions containing the object compound were combined and the solvent was evaporated under reduced pressure to give O-methyl-L-tyrosine (30 mg).

(b) Physical and chemical properties of O-methyl-L-tyrosine.
IR: (max) (Nujol): 3400, 3650–2250 (broad) 1675, 1615 cm$^{-1}$.

NMR (DCl-D$_2$O, δ): 7:2 (2H, d, J=8 Hz), 6.93 (2H, d, J=8 Hz), 4.33 (1H, t, J=6 Hz), 3.2 (2H, d, J=6 Hz).

$[\alpha]_D^{20}$: −8° (C=1, 1N-HCl).

From analysis of the above physico-chemical properties and further investigations for chemical structure, the chemical structure of FR-48736 substance has been elucidated as follows:

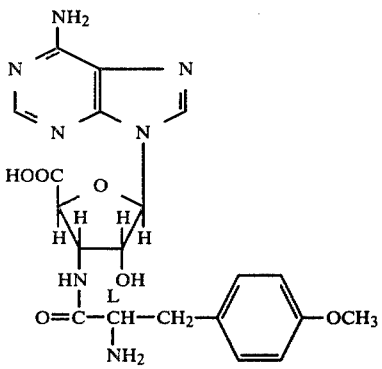

Fr-48736 substance 1-(6-Amino-9H—purin-9-yl)-1,3-dideoxy-
3-(O—methyl-L-tyrosylamino)-β-D—
ribofuranuronic acid The process for preparing the starting compounds of the present invention are explained in details in the following.

(1) PREPARATION 1

The compound (IIIb) or a salt thereof can be prepared by oxidizing the compound (IIIa).

Suitable oxidizing agent may include one which is applied for the transformation of a hydroxy group of sugar into a carboxy group of sugar acid such as alkali metal permanganate (e.g. sodium permanganate, potassium permanganate, etc.) or the like.

The present reaction is usually carried out in a conventional solvent which does not adversely influence the reaction such as water, tetrahydrofuran, etc. or a mixture thereof.

This reaction can be preferably conducted in the presence of a base (e.g. sodium hydroxide, potassium hydroxide, etc.).

The reaction temperature is not critical and the reaction is preferably carried out under warming to heating.

(2) PREPARATION 2

The compound (IIIc) can be prepared by esterifying the compound (IIIb) or a salt thereof.

This reaction may be conducted by a similar manner to that of Process 6.

(3) PREPARATION 3

The compound (IIId) can be prepared by subjecting the compound (IIIc) to elimination reaction of the hydroxy-protective group and then reacting the resulting compound with an acylating agent.

The elimination reaction can be conducted in a similar manner to that of Process 4 and the acylation reaction can be conducted in a similar manner to that of Process 2, respectively.

(4) PREPARATION 4

The compound (IIa) or a salt thereof can be prepared by reacting the compound (IIId) with the compound (IV) or a salt thereof.

This reaction can be preferably conducted by reacting the compound (IIId) with the silyl derivative of the compound (IV) in the presence of Lewis acid (e.g. stannic chloride, etc.).

This reaction is usually carried out in a solvent such as 1,2-dichloroethane or any other solvent which does not adversely affect the reaction. The reaction temperature is not critical, and the reaction is usually carried out under cooling to warming.

(5) PREPARATION 5

The compound (IIb) or a salt thereof can be prepared by subjecting the compound (IIa) or a salt thereof to deesterification reaction.

The reaction can be conducted in a similar manner to that of Process 7.

(6) PREPARATION 6

The compound (II) or a salt thereof can be prepared by subjecting the compound (IIc) or a salt thereof to deacylation reaction.

The reaction can be conducted in a similar manner to that of Process 3.

In the above Preparation 1 and Preparation 4 to 6, in case that the compound (IIIb), (IIa), (IIb), or (II) have free carboxy and/or free amino group(s), it may be transformed into its salt by a conventional method.

The object compound (I) or their pharmaceutically acceptable salts are useful for therapeutic treatment of infectious diseases caused by microorganisms especially by fungi in human being and animals.

For the purpose of showing such antimicrobial activities of the object compound (I) or their pharmaceutically acceptable salts, some pharmacological test data are illustrated in the following.

TEST 1

Antimicrobial activity test (in vitro):
Minimal inhibitory concentration (MIC) against Candida: (*Candida albicans* OUT6004)
Method: Pulp assay method
Medium: Malt agar

| Compounds (Example Nos.) | MIC (mcg/ml) |
|---|---|
| 39 | 31 |
| 55 | 31 |
| 73 | 31 |
| 98 (dihydro-chloride monohydrate) | 16 |

TEST 2

Antimicrobial activities of the compound in Example 98 [1-(6-amino-9H-purin-9-yl)-1,3-dideoxy-3-(O-methyl-L-tyrosylamino)-β-D-ribofuranuronic acid dihydrochloride monohydrate] against some species of Candida.

Minimal inhibitory concentration (MIC) against *Candida albicans*:
Method: Agar dilution method
Medium: Malt agar

| Strains | MIC (mcg/ml) |
|---|---|
| *Candida albicans* FP-614 | 0.8 |
| *Candida albicans* FP-616 | 0.2 |
| *Candida albicans* FP-618 | 0.8 |
| *Candida albicans* FP-620 | 0.2 |
| *Candida albicans* FP-622 | 3.1 |
| *Candida albicans* FP-633 | 1.6 |

TEST 3

Protective efficacy in experimental infection in mice:

In determining the protective efficacy against experimental infections of Candida in mice, the compound in Example 98 [1-(6-amino-9H-purin-9-yl)-1,3-dideoxy-3-(O-methyl-L-tyrosylamino)-β-D-ribofuranuronic acid dihydrochloride monohydrate] was suspended and diluted in sterile water to provide three concentrations of the drug for testing ddY-strains of mice aged 5 weeks and averaging 20 g in weight. Mice were used in groups of 5 mice each. One hour after the intravenous injection of $3.0 \times 10^6$ of Candida albicans FP-633 cells to each mouse, the drug solutions were administered subcutaneously or orally at the level mentioned below respectively.

One week after the infection, the test was considered complete and survival records of that day were made. The test results are shown below.

| Route | Dose (mg/kg) | Survival/infected |
|---|---|---|
| Subcutaneous | 15 | 4/5 |
|  | 5 | 1/5 |
| Oral | 30 | 3/5 |
|  | 10 | 1/5 |
| Control | — | 0/8 |

Toxicity:

Intraperitoneal administration of more than 1,000 mg/kg of 1-(6-amino-9H-purin-9-yl)-1,3-dideoxy-3-(O-methyl-L-tyrosylamino)-β-D-ribofuranuronic acid dihydrochloride monohydrate (the compound of Example 98) into mice did not result in any toxic symtom.

The antimicrobial composition of this invention can be used in the form of a pharmaceutical preparation, for example, in solid, semisolid or liquid form, which contains the object compound (I) or its pharmaceutically acceptable salts, as an active ingredient, in admixture with an organic or inorganic carrier or excipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, simisolid, or liquid form, and in addition auxiliary, stabilizing thickening and coloring agents and perfumes may be used. The active object compound is included in the pharmaceutical composition in an amount sufficient to produce the desired antimicrobial effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 1–200 mg of the active ingredient/kg of a human being or an animal is generally given for treating diseases, and an average single dose of about 50 mg, 100 mg, 250 mg, and 500 mg is generally administered.

The following examples are given for the purpose of illustrating the present invention.

PREPARATION 1

To a stirred suspension of 3-azido-3-deoxy-1,2-O-isopropylidene-α-D-ribofuranose (3.34 g) in a solution of potassium hydroxide (5.5 g) in water (200 ml) was added dropwise a solution of potassium permanganate (6.8 g) in water (200 ml) during 2 hours. The resulting suspension was stirred at ambient temperature for 1 hour. The precipitated manganese dioxide was removed by filtration and the filtrate was decolorized with sodium bisulfite and then acidified with 1N-hydrochloric acid. The solution was extracted with ethyl acetate (100 ml×3). The extract was washed with a saturated aqueous solution of sodium chloride (100 ml) and dried over magnesium sulfate. The solvent was removed under reduced pressure and the residue was recrystallized from a mixture of diethyl ether and n-hexane to give 3-azido-3-deoxy-1,2-O-isopropylidene-α-D-ribofuranuronic acid (2.937 g), mp. 56°–58° C. (from diethyl ether and n-hexane).

IR (CHCl$_3$): 3600–2400 (broad), 2990, 2820, 2130, 1720 cm$^{-1}$.

NMR (CDCl$_3$, δ): 9.13 (1H, s), 5.9 (1H, d, J=3.5 Hz), 4.73 (1H, t, J=3.5 Hz), 4.6 (1H, d, J=9 Hz), 3.7 (1H, dd, J=3.5, 9 Hz), 1.57 (3H, s), 1.37 (3H, s).

PREPARATION 2

A solution of 3-azido-3-deoxy-1,2-O-isopropylidene-α-D-ribofuranuronic acid (2.7 g) prepared in Preparation 1 in methanol (50 ml) was treated with excess ethereal diazomethane. After the reaction was completed, the solvent was evaporated under reduced pressure. The residue was chromatographed on a silica gel column and eluted with chloroform. The fractions containing the object compound were combined and the solvent was evaporated to give methyl 3-azido-3-deoxy-1,2-O-isopropylidene-α-D-ribofuranuronate (2.34 g) as colorless oil.

IR (CHCl$_3$): 2990, 2130, 1750 cm$^{-1}$.

NMR (CDCl$_3$, δ): 5.88 (1H, d, J=3.5 Hz), 4.73 (1H, t, J=3.5 Hz), 4.55 (1H, d, J=9 Hz), 3.83 (3H, s), 3.7 (1H, dd, J=3.5, 9 Hz), 1.57 (3H, s), 1.37 (3H, s).

PREPARATION 3

Methyl 3-azido-3-deoxy-1,2-O-isopropylidene-α-D-ribofuranuronate (2.29 g) prepared in Preparation 2 was added to 75% formic acid (200 ml), the mixture was heated at 50° C. for 2 hours, and the reaction mixture was evaporated under reduced pressure to dryness. The residue was dissolved and evaporated successively with n-butanol (50 ml×2) and toluene (50 ml×2). The residue was dissolved in a mixture of pyridine (20 ml) and acetic anhydride (12 ml), and allowed to stand at room temperature for 2 hours. The resultant mixture was poured onto crushed ice and extracted with chloroform (100 ml×3). The extracts were combined, washed with 1N-hydrochloric acid, saturated sodium bicarbonate and saturated sodium chloride, dried over magnesium sulfate and evaporated to dryness under reduced pressure.

The residue was chromatographed on a silica gel column and eluted with a mixture of n-hexane and ethyl acetate (7:3). The fractions containing the object compound were combined and the solvent was evaporated to give methyl 3-azido-3-deoxy-1,2-di-O-acetyl-D-ribofuranuronate (2.27 g) as syrup. The 1H-NMR spectrum suggested that this syrup consists of two diastereoisomers at the anomeric center and that the anomer having β-configuration is almost exclusively predominant.

IR (CHCl$_3$): 3030, 2950, 2130, 1750 cm$^{-1}$.

NMR (CDCl$_3$, δ): 6.17 (1H, s), 5.3 (1H, d, J=4 Hz) 4.63–4.2 (2H, m), 3.8 (3H, s), 2.17 (3H, s), 2.07 (3H, s).

PREPARATION 4

A suspension of N$^6$-benzoyladenine (552 mg) in hexamethyldisilazane (10 ml) and chlorotrimethylsilane (0.6 ml) was refluxed for 3 hours. Excess hexamethyldisilazane was removed under reduced pressure from the resultant clear solution. To the residue, dissolved in 1,2-dichloroethane (10 ml), were added a solution of methyl 3-azido-3-deoxy-1,2-di-O-acetyl-D-ribofuranuronate (500 mg) prepared in Preparation 3 in 1,2-dichloroethane (5 ml) and stannic chloride (0.5 ml). The mixture was stirred at 60°–70° C. for 4 hours and then was poured onto crushed ice. The resultant mixture was extracted with chloroform (20 ml×3). The extracts were combined, washed with saturated sodium bicarbonate and saturated sodium chloride, dried over magnesium sulfate and evaporated to dryness under reduced pressure. The residue was chromatographed on a silica gel column and eluted with a mixture of chloroform and methanol (93:7). The fractions, containing the desired compound, were combined and the solvent was evaporated to give methyl-2-O-acetyl-3-azido-1-(6-benzoylamino-9H-purin-9-yl)-1,3-dideoxy-β-D-ribofuranuronate (450 mg) as syrup.

IR (CHCl$_3$): 3120, 3000, 2130, 1750, 1640 cm$^{-1}$.

NMR (CDCl$_3$, δ): 8.97 (1H, s), 8.7 (1H, s), 8.4 (1H, s), 8.1–7.7 (2H, m), 7.6–7.2 (3H, m), 6.3 (1H, d, J=5 Hz), 5.84 (1H, t, J=5 Hz), 4.87 (1H, t, J=5 Hz), 4.6 (1H, d, J=5 Hz), 3.8 (3H, s), 2.13 (3H, s).

PREPARATION 5

Methyl 2-O-acetyl-3-azido-1-(6-benzoylamino-9H-purin-9-yl)-1,3-dideoxy-β-D-ribofuranuronate (280 mg) prepared in Preparation 4 was dissolved in 0.5N sodium hydroxide (20 ml) and the solution was stirred for 30 minutes at room temperature, which contained 3-azido-1-(6-benzoylamino-9H-purin-9-yl)-1,3-dideoxy-β-D-ribofuranuronic acid.

PREPARATION 6

A solution of methyl 1-(6-benzoylamino-9H-purin-9-yl)-2-O-acetyl-3-azido-1,3-dideoxy-β-D-ribofuranuronate (1.10 g) prepared in Preparation 4 in 0.5N aqueous sodium hydroxide (25 ml) was stirred for 30 minutes. The solution was adjusted to pH 1 with 10% hydrochloric acid and extracted with ethyl acetate. After the extract was washed with brine, a solution of diazomethane in diethyl ether was dropped thereto until the yellow color was not disappeared. The solution was dried over magnesium sulfate and evaporated to dryness. The residue was triturated in diethyl ether to give methyl 1-(6-benzoylamino-9H-purin-9-yl)-3-azido-1,3-dideoxy-β-D-ribofuranuronate (433 mg).

IR (nujol): 3800–3000, 2140, 1750, 1702, 1616, 1588, 1515, 1255, 1220, 1180, 1102, 1077, 1030, 1000 cm$^{-1}$.

NMR (CDCl$_3$, δ): 2.33 (1H, m), 3.83 (3H, s), 4.42–4.68 (2H, m), 5.14 (1H, t, J=6 Hz), 6.00 (1H, m), 6.27 (1H, d, J=6 Hz), 7.38–7.63 (3H, m), 7.89–8.02 (2H, m), 8.51 (2H, s) 9.23 (1H, m).

PREPARATION 7

(1) Diphenyldiazomethane (5.87 g) was added to a solution of N-tert-butoxycarbonyl-L-tyrosine (5.00 g ) in tetrahydrofuran (50 ml) at room temperature. After standing overnight, acetic acid (7.15 ml) was added thereto, stood for another 2 hours and then evaporated to dryness. The residue in water was extracted with ethyl acetate. The extract was washed with an aqueous solution of sodium bicarbonate, dried over magnesium sulfate and evaporated to dryness. The residue was triturated in diethyl ether to give diphenylmethyl ester of N-tert-butoxycarbonyl-L-tyrosine (6.00 g).

NMR (DMSO-d$_6$+D$_2$O, δ): 1.33 (9H, s), 2.85 (2H, d, J=6 Hz), 4.20 (1H, m), 6.60 (2H, d, J=9 Hz), 6.77 (1H, s), 7.00 (2H, d, J=9 Hz), 7.30 (10H, s).

(2) A mixture of diphenylmethyl ester of N-tert-butoxycarbonyl-L-tyrosine (447 mg) prepared in Preparation 7 (1), N-(3-bromopropyl)phthalimide (644 mg) and potassium tert-butoxide (268 mg) in dimethyl sulfoxide (7 ml) was stirred for 6 hours at room temperature. The reaction mixture was diluted with water, and extracted with diethyl ether. The extract was washed with water and brine, dried, and evaporated to dryness to give diphenylmethyl ester of N-tert-butoxycarbonyl-O-(3-phthalimidopropyl)-L-tyrosine quantitatively as oil.

IR (Film): 3360, 1770, 1720–1690, 1610, 1510, 1490 cm$^{-1}$.

(3) A mixture of diphenylmethyl ester of N-tert-butoxycarbonyl-O-(3-phthalimidopropyl)-L-tyrosine (4.4 g) and hydrazine hydrate (0.52 g) in ethanol (50 ml) was heated under reflux for 2.5 hours. After cooling, the resulting precipitates were filtered off and the filtrate was concentrated under reduced pressure. The residue was diluted with water and extracted with ethyl acetate. The extract was washed with water and brine, dried and evaporated to dryness to give diphenylmethyl ester of N-tert-butoxycarbonyl-O-(3-aminopropyl)-L-tyrosine (2.5 g) as oil.

IR (Film): 3400–3200, 1740–1680, 1640, 1610 cm$^{-1}$.

(4) A mixture of diphenylmethyl ester of N-tert-butoxycarbonyl-O-(3-aminopropyl)-L-tyrosine (2.35 g) 1N sodium hydroxide (9.3 ml) and dioxane (5 ml) was stirred for 4.5 hours at room temperature, and di-tert-butyl dicarbonate (1.30 g) was added thereto. The mixture was stirred for 1 hour at room temperature, evaporated, diluted with water, and washed with diethyl ether. The aqueous layer was acidified with 1N hydrochloric acid and extracted with diethyl ether. The extract was washed with water and brine, dried and then evaporated to dryness to given N-tert-butoxycarbonyl-O-(3-tert-butoxycarbonylaminopropyl)-L-tyrosine (1.28 g) as oil.

IR (Film): 3300, 2700–2300, 1720–1680, 1510 cm$^{-1}$.

PREPARATION 8

(1) A mixture of diphenylmethyl ester of N-tert-butoxycarbonyl-L-tyrosine (5.00 g), methyl chloroacetate (1.45 g) and potassium carbonate (1.85 g) in N,N-dimethylformamide (75 ml) was stirred for 20 hours at room temperature. The mixture was diluted with water (100 ml) and extracted with ethyl acetate. The extract was washed with diluted hydrochloric acid, aqueous sodium bicarbonate, and then brine. After dried over magnesium sulfate, the extract was evaporated to dryness to give diphenylmethyl ester of N-tert-butoxycarbonyl-O-methoxycarbonylmethyl-L-tyrosine (6.40 g), mp. 69°–73° C.

IR (nujol): 3400, 3350, 1760, 1740, 1690, 1520, 1440, 1280, 1250, 1210, 1180, 1160, 1080, 1060, 740, 700 cm$^{-1}$.

NMR (CDCl$_3$, δ): 1.38 (9H, s), 3.02 (2H, d, J=6 Hz), 3.75 (3H, s), 4.5–5.2 (2H, m), 4.52 (2H, s), 6.65 (2H, d, J=8 Hz), 6.87 (2H, d, J=8 Hz), 6.88 (1H, s), 7.30 (10H, s).

(2) A mixture of diphenyl methyl ester of N-tert-butoxycarbonyl-O-methoxycarbonylmethyl-L-tyrosine (3.0 g) and 10% palladium-charcoal (1.5 g) in methanol (130 ml) and water (20 ml) was hydrogenated at 3 atmospheric pressure for 2 hours at room temperature. After the catalyst was filtered off, the filtrate was evaporated. The residue was adjusted to pH 7 with aqueous sodium bicarbonate and washed with diethyl ether. The aqueous layer was acidified with 6N hydrochloric acid and extracted with ethyl acetate. The extract was washed with brine, dried over magnesium sulfate, and then evaporated to dryness to give N-tert-butoxycarbonyl-O-methoxycarbonylmethyl-L-tyrosine (1.9 g), mp. 75°–79° C.

IR (CHCl$_3$): 3400, 2950, 1760–1690, 1500, 1170 cm$^{-1}$.

EXAMPLE 1

To the whole reaction mixture prepared in Preparation 5 which contains 3-azido-1-(6-benzoylamino-9H-purin-9-yl)-1,3-dideoxy-β-D-ribofuranuronic acid was added 1N hydrochloric acid to adjust to pH 2. The mixture was hydrogenated under medium pressure (3.0–3.5 atm) over palladium black (50 mg) at room temperature for 1 hour.

The catalyst was removed by filtration and the filtrate was adjusted to pH 7 with 1N sodium hydroxide. The resulting solution was applied to a column of Diaion HP-20 (trade mark, Mitsubishi Chemical Industries Ltd.) (20 ml), and the column was washed with water (40 ml) and then eluted with a mixture of methanol and water (1:1)(60 ml). The solvent was evaporated under reduced pressure and the residue was recrystallized from water to give 3-amino-1-(6-benzoylamino-9H-purin-9-yl)-1,3-dideoxy-β-D-ribofuranuronic acid (170 mg), mp. 220°–225° C. (dec.)(from water).

IR (nujol): 3600–2200 (broad), 1685, 1640, 1620 cm$^{-1}$.

NMR (D$_2$O-DCl, δ): 9.05 (1H, s), 8.97 (1H, s), 8.2–7.8 (2H, m), 7.8–7.3 (3H, m), 6.57 (1H, d, J=2 Hz), 5.23 (1H, dd, J=2, 6 Hz).

EXAMPLE 2

To a stirred solution of N-benzyloxycarbonyl-O-methyl-L-tyrosine (181 mg) and N-hydroxysuccinimide (64 mg) in dioxane (10 ml) was added N,N'-dicyclohexylcarbodiimide (114 mg) under cooling in an ice bath. The mixture was stirred overnight at room temperature. The suspension was filtered and the filtrate was evaporated to dryness under reduced pressure. The residue was dissolved in tetrahydrofuran (5 ml) and the solution was added to a solution of 3-amino-1-(6-benzoylamino-9H-purin-9-yl)-1,3-dideoxy-β-D-ribofuranuronic acid (150 mg) prepared in Example 1 and triethylamine (0.08 ml) in water (5 ml). The mixture was stirred for a day at room temperature. Tetrahydrofuran was evaporated under reduced pressure and the residual aqueous solution was adjusted to pH 2 with 1N hydrochloric acid and extracted with ethyl acetate (30 ml×3). The extracts were combined, washed with saturated sodium chloride, dried over magnesium sulfate and evaporated to dryness under reduced pressure. The residue was subjected to column chromatography on silica gel and eluted with a mixture of chloroform and methanol (8:2). The fractions containing the object compound were combined and the solvent was evaporated under reduced pressure to give 1-(6-benzoylamino-9H-purin-9-yl)-3-(N-benzyloxycarbonyl-O-methyl-L-tyrosylamino)-1,3-dideoxy-β-D-ribofuranuronic acid (150 mg) as syrup.

IR (nujol): 3700–2100 (broad), 1700, 1675, 1640, 1610 cm$^{-1}$.

NMR (DMSO-d$_6$-D$_2$O, δ): 9.4 (1H, s), 8.63 (1H, s), 8.1–7.8 (2H, m), 7.75–6.97 (10H, m), 6.7 (2H, d, J=8 Hz), 6.23 (1H, d, J=2 Hz), 4.87 (2H, m), 4.7–4.07 (4H, m) 3.63 (3H, s).

EXAMPLE 3

A suspension of 1-(6-benzoylamino-9H-purin-9-yl)-3-(N-benzyloxycarbonyl-O-methyl-L-tyrosylamino)-1,3-dideoxy-β-D-ribofuranuronic acid (300 mg) prepared in Example 2 in a mixture of methanol (20 ml) and n-butylamine (10 ml) was boiled under reflux for 1 hour. The mixture was evaporated under reduced pressure. The residue was subjected to column chromatography on silica gel and eluted with a mixture of chloroform and methanol (7:3). The fractions containing the object compound were combined and the solvent was evaporated to give 1-(6-amino-9H-purin-9-yl)-3-(N-benzyloxycarbonyl-O-methyl-L-tyrosylamino)-1,3-dideoxy-β-D-ribofuranuronic acid (200 mg).

IR (nujol): 3650–2450, 1685, 1650, 1635, 1610 cm$^{-1}$.

NMR (CDCl$_3$:CD$_3$OD=1:1, δ): 8.8 (1H, s), 8.13 1 (1H, s), 7.2 (5H, s), 7.07 (2H, d, J=8 Hz), 6.7 (2H, d, J=8 Hz), 6.08 (1H, d, J=2 Hz), 4.94 (2H, s), 3.7 (3H, s), 2.98 (2H, d, J=7 Hz).

EXAMPLE 4

A suspension of 1-(6-amino-9H-purin-9-yl)-3-(N-benzyloxycarbonyl-O-methyl-L-tyrosylamino)-1,3-dideoxy-β-D-ribofuranuronic acid (150 mg) prepared in Example 3 in water (200 ml) was adjusted to pH 3 with 1N hydrochloric acid. The resulting mixture was hydrogenated under medium pressure (3.0–3.5 atm.) over palladium black (30 mg) for 3 hours. The catalyst was removed by filtration and the filtrate was adjusted to pH 7 with 1N sodium hydroxide. The resulting mixture was concentrated under reduced pressure to a volume of 30 ml. The concentrate was applied to a column of non ionic adsorption resin "HP-20" (trade mark, Mitsubishi Chemical Industries, Ltd.) (50 ml) and the column was washed with water (100 ml) and then eluted with a mixture of methanol and water (3:7)(100 ml). The solvent was evaporated under reduced pressure and the residue was crystallized from 0.1N hydrochloric acid to give 1-(6-amino-9H-purin-9-yl)-1,3-dideoxy-3-(O-methyl-L-tyrosylamino)-β-D-ribofuranuronic acid dihydrochloride monohydrate (60 mg), mp. 215°–230° C. (dec.).

IR (KBr): 3600–2200, 1720(sh), 1695, 1665, 1630, 1610, 1560 cm$^{-1}$.

NMR (DCl-D$_2$O, δ): 8.62 (1H, s), 8.47 (1H, s), 7.35 (2H, d, J=8 Hz), 7.03 (2H, d, J=8 Hz), 6.25 (1H, d, J=3 Hz), 5.3–4.8 (2H, m), 4.8–4.0 (2H, m), 3.84 (3H, s), 3.22 (2H, d, J=7 Hz).

$[α]_D^{20} = +33°$ (C=1, 1N-HCl)

Elemental Analysis (C$_{20}$H$_{23}$N$_7$O$_6$·2HCl·H$_2$O)

|  | C | H | N | Cl |
|---|---|---|---|---|
| calculated: | 43.80 | 4.96 | 17.88 | 12.93 |
| found: | 44.06 | 5.03 | 18.12 | 12.64 |

EXAMPLE 5

To a solution of 1-(6-benzoylamino-9H-purin-9-yl)-1,3-dideoxy-3-amino-β-D-ribofuranuronic acid (384 mg) prepared in Example 1 and triethylamine (0.19 ml) in water (10 ml) was added a solution of N-hydroxysuccinimide ester of N-benzyloxycarbonyl-L-phenylalanine (635 mg) in tetrahydrofuran (10 ml) at room temperature under stirring, which was continued overnight. The mixture was evaporated to remove tetrahydrofuran, acidified with 10% hydrochloric acid and extracted with ethyl acetate. The extract was washed with brine, dried over magnesium sulfate and evaporated to dryness. The residue was triturated in diethyl ether to give 1-(6-benzoylamino-9H-purin-9-yl)-1,3-dideoxy-3-(N-benzyloxycarbonyl-L-phenylalanylamino)-β-D-ribofuranuronic acid (521 mg), mp. 145°–150° C. (dec.).

IR (Nujol): 3275, 1700, 1610, 1580, 1510, 1250, 1170, 1090, 1070 cm$^{-1}$.

NMR (DMSO-d$_6$, δ): 2.7–3.1 (2H, m), 4.2–4.5 (2H, m), 4.78 (2H, m), 4.90 (2H, s), 6.26 (1H, s), 7.23 (12H, s), 7.4–7.6 (3H, m), 7.8–8.1 (2H, m), 8.44 (1H, m), 8.71 (1H, s), 8.78 (1H, s).

EXAMPLE 6

1-(6-Benzoylamino-9H-purin-9-yl)-1,3-dideoxy-3-(N-benzyloxycarbonyl-D-phenylalanylamino)-β-D-ribofuranuronic acid (405 mg) was prepared by reacting 1-(6-benzoylamino-9H-purin-9-yl)-1,3-dideoxy-3-amino-β-D-ribofuranuronic acid (384 mg) prepared in Example 1 with N-hydroxysuccinimide ester of N-benzyloxycarbonyl-D-phenylalanine (543 mg) according to a similar manner to that of Example 5, mp. 206°–210° C. (dec.).

IR (Nujol): 3550, 3320, 1685, 1655, 1610, 1585, 1530, 1340, 1285, 1240, 1215, 1195, 1175, 1100, 1085, 1070 cm$^{-1}$.

NMR (DMSO-d$_6$, δ): 2.67–3.15 (2H, m), 4.34–4.63 (2H, m), 4.63–4.95 (2H, m), 4.95 (2H, s), 6.31 (2H, m), 7.26 (11H, s), 7.49–7.60 (3H, m), 7.93–8.13 (2H, m), 8.39 (1H, m), 8.75 (1H, s), 8.82 (1H, s).

EXAMPLE 7

1-(6-Benzoylamino-9H-purin-9-yl)-1,3-dideoxy-3-(D,L-3-tert-butoxycarbonylamino-3-phenylpropionylamino)-β-D-ribofuranuronic acid (362 mg) was prepared by reacting 1-(6-benzoylamino-9H-purin-9-yl)-1,3-dideoxy-3-amino-β-D-ribofuranuronic acid (300 mg) prepared in Example 1 with N-hydroxysuccinimide ester of D,L-3-tert-butoxycarbonylamino-3-phenylpropionic acid (310 mg) according to a similar manner to that of Example 5, mp. 158°–162° C. (dec.).

IR (nujol): 3300, 1680, 1645, 1610, 1585, 1520, 1290, 1245, 1220, 1170, 1090, 1075, 1020 cm$^{-1}$.

NMR (DMSO-d$_6$, δ): 1.31 (9H, s), 4.38 (2H, m), 4.58–4.98 (2H, m), 6.09 (1H, m), 6.24 (1H, m), 7.28 (6H, s), 7.42–7.81 (3H, m), 7.88–8.08 (3H, m), 8.72–8.76 (2H, m).

EXAMPLE 8

1-(6-Benzoylamino-9H-purin-9-yl)-3-(N-tert-butoxycarbonyl-D,L-phenylglycylamino)-1,3-dideoxy-β-D-ribofuranuronic acid (299 mg) was prepared by reacting 1-(6-benzoylamino-9H-purin-9-yl)-1,3-dideoxy-3-amino-β-D-ribofuranuronic acid (384 mg) prepared in Example 1 with N-hydroxysuccinimide ester of N-tert-butoxycarbonyl-D,L-phenylglycine (382 mg) according to a similar manner to that of Example 5, mp. 85°–92° C.

IR (nujol): 3350, 1690, 1570, 1250, 1160, 1090 cm$^{-1}$.

NMR (DMSO-d$_6$+D$_2$O, δ): 1.40 (9H, s), 4.3–4.5 (1H, m), 4.5–4.9 (2H, m), 5.4 (1H, bs), 6.3 (1H, m), 7.2–7.5 (5H, m), 7.5–7.8 (3H, m), 7.9–8.2 (2H, m), 8.8 (2H, bs)

EXAMPLE 9

1-(6-Benzoylamino-9H-purin-9-yl)-3-[N-tert-butoxycarbonyl-β-(4-fluorophenyl)-D,L-alanylamino]-1,3-dideoxy-β-D-ribofuranuronic acid (575 mg) was prepared by reacting 1-(6-benzoylamino-9H-purin-9-yl)-1,3-dideoxy-3-amino-β-D-ribofuranuronic acid (384 mg) prepared in Example 1 with N-hydroxysuccinimide ester of N-tert-butoxycarbonyl-β-(4-fluorophenyl)-D,L-alanine (417 mg) according to a similar manner to that of Example 5, mp. 125°–134° C. (dec.).

IR (nujol): 3250, 1690, 1610, 1510, 1250, 1220, 1160, 1090, 1060 cm$^{-1}$.

NMR (DMSO-d$_6$+D$_2$O, δ): 1.25 (9H, s), 2.7–3.1 (2H, m), 4.0–4.2 (1H, m), 4.2–4.6 (1H, m), 4.6–4.8 (2H, m), 6.3 (1H, m), 6.9–7.4 (4H, m), 7.4–7.7 (3H, m), 7.9–8.2 (2H, m), 8.70 (1H, s), 8.93 (1H, s)

EXAMPLE 10

1-(6-Benzoylamino-9H-purin-9-yl)-3-(N-tert-butoxycarbonyl-O-methyl-β-phenyl-D,L-erythroserylamino)-1,3-dideoxy-β-D-ribofuranuronic acid (360 mg) was prepared by reacting 1-(6-benzoylamino-9H-9-yl)-1,3-dideoxy-3-amino-β-D-ribofuranuronic acid (384 mg) prepared in Example 1 with N-hydroxysuccinimide ester of N-tert-butoxycarbonyl-O-methyl-β-phenyl-D,L-erythroserine (431 mg) according to a similar manner to that of Example 5, mp. 164°–166° C. (dec.).

IR (nujol): 3300, 1690, 1650, 1610, 1580, 1510, 1250, 1220, 1170, 1090 cm$^{-1}$.

NMR (DMSO-d$_6$+D$_2$O, δ): 1.18 (9H, s), 3.09 (3H, s), 4.0–4.6 (3H, m), 4.6–4.9 (2H, m), 6.3 (1H, m), 7.30 (5H, s), 7.4–7.7 (3H, m), 7.8–8.2 (2H, m), 8.70 (1H, s), 8.72 (1H, s).

EXAMPLE 11

1-(6-Benzoylamino-9H-purin-9-yl)-3-(N$^α$,N$^ε$-dibenzyloxycarbonyl-L-lysylamino)-1,3-dideoxy-β-D-ribofuranuronic acid (420 mg) was prepared by reacting 1-(6-benzoylamino-9H-purin-9-yl)-1,3-dideoxy-3-amino-β-D-ribofuranuronic acid (384 mg) prepared in Example 1 with N-hydroxysuccinimide ester of N$^α$,N$^ε$-dibenzyloxycarbonyl-L-lysine (608 mg) according to a similar manner to that of Example 5, mp. 150°–157° C. (dec.).

IR (nujol): 3300, 1720, 1710, 1685, 1655, 1610, 1585, 1530, 1245, 1090 cm$^{-1}$.

NMR (DMSO-d$_6$+D$_2$O, δ): 1.0–1.9 (6H, m), 2.9–3.1 (2H, m), 4.2 (1H, m), 4.5 (1H, m), 4.8 (1H, m), 6.34 (1H, m), 7.42 (10H, s), 7.4–7.8 (3H, m), 8.0–8.2 (2H, m), 8.82 (1H, s), 8.87 (1H, s).

EXAMPLE 12

1-(6-Benzoylamino-9H-purin-9-yl)-3-(N-benzyloxycarbonyl-O-benzyl-L-tyrosylamino)-1,3-dideoxy-β-D-ribofuranuronic acid (210 mg) was prepared by reacting 1-(6-benzoylamino-9H-purin-9-yl)-1,3-dideoxy-3-amino-β-D-ribofuranuronic acid (200 mg) prepared in Example 1 with N-hydroxysuccinimide ester of N-benzyloxycarbonyl-O-benzyl-L-tyrosine (260 mg) according to a similar manner to that of Example 5, mp. 150°-155° C.

IR (nujol): 3320, 1695, 1660, 1610, 1590, 1515, 1240, 1090 cm$^{-1}$.

NMR (DMSO-d$_6$+D$_2$O, δ): 2.95 (2H, m), 4.00 (1H, m), 4.2–4.6 (2H, m), 4.80 (1H, m), 4.95 (2H, s), 5.07 (2H, s), 6.30 (1H, d, J=2 Hz), 7.26 (5H, s), 7.38 (5H, s), 6.8–8.5 (9H, m), 8.75 (1H, s), 8.82 (1H, s).

EXAMPLE 13

1-(6-Benzoylamino-9H-purin-9-yl)-3-(N-benzyloxycarbonyl-L-alanylamino)-1,3-dideoxy-β-D-ribofuranuronic acid (310 mg) was prepared by reacting 1-(6-benzoylamino-9H-purin-9-yl)-1,3-dideoxy-3-amino-β-D-ribofuranuronic acid (300 mg) prepared in Example 1 with N-hydroxysuccinimide ester of N-benzyloxycarbonyl-L-alanine (300 mg) according to a similar manner to that of Example 5, mp. 154°-156° C.

IR (Nujol): 3300, 1715, 1660, 1618, 1590, 1530 cm$^{-1}$.

NMR (DMSO-d$_6$+D$_2$O, δ): 1.26 (3H, d, J=7 Hz), 4.16 (1H, m), 4.43 (1H, m), 4.72 (2H, m), 5.01 (2H, s), 6.24 (1H, d, J=2 Hz), 7.29 (5H, s), 7.5–8.4 (5H, m), 8.72 (1H, s), 8.75 (1H, s).

EXAMPLE 14

1-(6-Benzoylamino-9H-purin-9-yl)-3-(N-benzyloxycarbonyl-β-alanylamino)-1,3-dideoxy-β-D-ribofuranuronic acid (590 mg) was prepared by reacting 1-(6-benzoylamino-9H-purin-9-yl)-1,3-dideoxy-3-amino-β-D-ribofuranuronic acid (384 mg) prepared in Example 1 with N-hydroxysuccinimide ester of N-benzyloxycarbonyl-β-alanine (450 mg) according to a similar manner to that of Example 5, mp. 136°-141° C.

IR (nujol): 3300, 1710, 1690, 1650, 1615, 1590, 1550–1510 cm$^{-1}$.

NMR (DMSO-d$_6$+D$_2$O, δ): 2.47 (2H, t, J=7 Hz), 3.10 (2H, t, J=7 Hz), 4.47 (1H, d, J=6 Hz), 4.77 (2H, m), 5.08 (2H, s), 6.25 (1H, d, J=2 Hz), 7.30 (5H, s), 7.5–8.2 (5H, m), 8.70 (2H, bs).

EXAMPLE 15

1-(6-Benzoylamino-9H-purin-9-yl)-3-[N-(N-benzyloxycarbonylglycyl)-O-methyl-L-tyrosylamino]-1,3-dideoxy-β-D-ribofuranuronic acid (550 mg) was prepared by reacting 1-(6-benzoylamino-9H-purin-9-yl)-1,3-dideoxy-3-amino-β-D-ribofuranuronic acid (300 mg) prepared in Example 1 with N-hydroxysuccinimide ester of N-(N-benzyloxycarbonylglycyl)-O-methyl-L-tyrosine (415 mg) according to a similar manner to that of Example 5, mp. 78°-84° C.

IR (nujol): 3300, 1700, 1650, 1510, 1245, 1175, 1025 cm$^{-1}$.

NMR (DMSO-d$_6$, δ): 3.53–3.79 (2H, m), 3.68 (3H, s), 4.41–4.93 (4H, m), 5.01 (2H, s), 6.17 (2H, broad s), 6.32 (1H, m), 6.77 (2H, d, J=8 Hz), 7.01–7.61 (7H, m), 7.30 (5H, s), 7.98–8.10 (2H, m), 8.77 (1H, s), 8.91 (1H, s).

EXAMPLE 16

1-(6-Benzoylamino-9H-purin-9-yl)-3-[2-(4-nitrobenzyloxycarbonyl)-2-phenylacetylamino]-1,3-dideoxy-β-D-ribofuranuronic acid (315 mg) was prepared by reacting 1-(6-benzoylamino-9H-purin-9-yl)-1,3-dideoxy-3-amino-β-D-ribofuranuronic acid (300 mg) prepared in Example 1 with N-hydroxysuccinimide ester of 2-(4-nitrobenzyloxycarbonyl)-2-phenylacetic acid (386 mg) according to a similar manner to that of Example 5, mp. 168°-175° C. (dec.).

IR (nujol): 3370, 3200, 1740, 1685, 1645, 1585, 1545, 1520, 1505, 1403, 1323, 1250, 1230, 1155, 1080, 1005 cm$^{-1}$.

NMR (DMSO-d$_6$, δ): 4.24–4.57 (1H, m), 4.74 (2H, m), 5.10 (1H, s), 5.28 (2H, s), 6.25 (1H, d, J=2 Hz), 7.23–7.62 (11H, m), 7.93–8.24 (5H, m), 8.72 (1H, s), 8.80 (1H, s), 8.80 (1H, m).

EXAMPLE 17

To a mixture of 1-(6-benzoylamino-9H-purin-9-yl)-1,3-dideoxy-3-amino-β-D-ribofuranuronic acid (384 mg) prepared in Example 1 and triethylamine (0.35 ml) in water (10 ml) was dropped a solution of phenylacetyl chloride (0.171 g) in tetrahydrofuran (10 ml) under cooling in an ice bath and stirring, which was continued for 30 minutes at the same temperature. The mixture was evaporated to remove tetrahydrofuran and the remaining aqueous solution was washed with diethyl ether and acidified with 6N hydrochloric acid. The mixture was extracted with a mixture (80 ml) of ethanol-chloroform (1:1) and the extract was dried over magnesium sulfate, evaporated and triturated with diethyl ether to give 1-(6-benzoylamino-9H-purin-9-yl)-3-(phenylacetylamino)-1,3-dideoxy-β-D-ribofuranuronic acid (370 mg), mp. 135°-140° C. (dec.).

IR (Nujol): 3300, 1710, 1645, 1600, 1580, 1450, 1240, 1220, 1080, 1060 cm$^{-1}$.

NMR (DMSO-d$_6$+D$_2$O, δ): 3.62 (2H, s), 4.5–4.6 (1H, m), 4.7–4.9 (2H, m), 6.3 (1H, m), 7.37 (5H, s), 7.5–7.8 (3H, m), 7.9–8.2 (2H, m), 8.87 (1H, s), 8.97 (1H, s).

EXAMPLE 18

1-(6-Benzoylamino-9H-purin-9-yl)-3-(3-phenylpropionylamino)-1,3-dideoxy-β-D-ribofuranuronic acid (490 mg) was prepared by reacting 1-(6-benzoylamino-9H-purin-9-yl)-1,3-dideoxy-3-amino-β-D-ribofuranuronic acid (250 mg) prepared in Example 1 with 3-phenylpropionyl chloride (132 mg) according to a similar manner to that of Example 17.

NMR (DMSO-d$_6$, δ): 2.76–3.43 (4H, m), 4.42–4.86 (3H, m), 6.31 (1H, m), 7.22 (6H, s), 7.55–7.73 (3H, m), 8.00–8.15 (2H, m), 8.39 (1H, d), 8.83 (1H, m), 9.09 (1H, s).

EXAMPLE 19

1-(6-Benzoylamino-9H-purin-9-yl)-3-benzoylamino-1,3-dideoxy-β-D-ribofuranuronic acid (125 mg) was prepared by reacting 1-(6-benzoylamino-9H-purin-9-yl)-1,3-dideoxy-3-amino-β-D-ribofuranuronic acid (250 mg) prepared in Example 1 with benzoyl chloride (110 mg) according to a similar manner to that of Example 17, mp. 112°-118° C. (dec.).

IR (nujol): 3250, 1695, 1645, 1610, 1580, 1520, 1250, 1176, 1065, 1023 cm$^{-1}$.

NMR (DMSO-d$_6$, δ): 4.95 (2H, m), 5.13 (1H, m), 6.32 (1H, m), 6.43 (1H, d, J=2 Hz), 7.58 (6H, m), 8.07 (4H, m), 8.75 (1H, s), 8.85 (1H, s), 9.01 (1H, s).

EXAMPLE 20

1-(6-Amino-9H-purin-9-yl)-3-cinnamoylamino-1,3-dideoxy-β-D-ribofuranuronic acid (135 mg) was prepared by reacting 1-(6-amino-9H-purin-9-yl)-1,3-dideoxy-3-amino-β-D-ribofuranuronic monohydrate (150 mg) prepared in Example 99 with cinnamoyl chloride (94 mg) according to a similar manner to that of Example 17, mp. 179°–185° C. (dec.).

IR (nujol): 3300, 1690, 1650, 1610, 1210, 1080 cm$^{-1}$.

NMR (DMSO-d$_6$+D$_2$O, δ): 4.2–4.9 (3H, m), 6.1 (1H, m), 6.82 (1H, d, J=16 Hz), 7.47 (1H, d, J=16 Hz), 7.1–7.6 (5H, m), 8.17 (1H, s), 8.55 (1H, s).

EXAMPLE 21

1-(6-Amino-9H-purin-9-yl)-1,3-dideoxy-3-(N-formyl-L-phenylalanylamino)-β-D-ribofuranuronic acid (58 mg) was prepared by reacting 1-(6-amino-9H-purin-9-yl)-1,3-dideoxy-3-amino-β-D-ribofuranuronic acid monohydrate (140 mg) prepared in Example 99 with N-hydroxysuccinimide ester of N-formyl-L-phenylalanine (130 mg) according to a similar manner to that of Example 5, mp. 169°–181° C. (dec.).

IR (nujol): 3350, 3250, 1685, 1650, 1500, 1220, 1090 cm$^{-1}$.

NMR (DMSO-d$_6$+D$_2$O, δ): 2.92–3.24 (2H, m), 3.84–4.95 (4H, m), 6.05 (1H, m), 7.19 (5H, s), 7.84 (1H, m), 8.14 (1H, m), 8.36 (1H, m).

EXAMPLE 22

1-(6-Benzoylamino-9H-purin-9-yl)-3-D-mandelylamino-1,3-dideoxy-β-D-ribofuranuronic acid (300 mg) was prepared by reacting 1-(6-benzoylamino-9H-purin-9-yl)-1,3-dideoxy-3-amino-β-D-ribofuranuronic acid (300 mg) prepared in Example 1 with 2,4-dioxo-5-phenyl-1,3-dioxolane (253 mg), prepared from D-mandelic acid, according to a similar manner to that of Example 5, mp. 223°–227° C. (dec.).

IR (nujol): 3440, 3310, 3200, 1705, 1645, 1605, 1590, 1520, 1400, 1360, 1330, 1295, 1280, 1240, 1220, 1205, 1180, 1140, 1100, 1090, 1080, 1065 cm$^{-1}$.

NMR (DMSO-d$_6$, δ): 4.43–4.65 (1H, m), 4.56 (1H, m), 4.78 (2H, m), 5.01 (1H, m), 6.25 (1H, d, J=2 Hz), 6.25–6.72 (1H, m), 7.19–7.44 (5H, m), 7.44–7.65 (3H, m), 7.90–8.22 (3H, m), 8.71 (1H, s), 8.76 (1H, s).

EXAMPLE 23

A mixture of 1-(6-benzoylamino-9H-purin-9yl)-1,3-dideoxy-3-(N-benzyloxycarbonyl-L-phenylalanylamino)-β-D-ribofuranuronic acid (432 mg) prepared in Example 5 and n-butylamine (3.5 ml) in methanol (15 ml) was refluxed for 50 minutes and evaporated to dryness. The residue was dissolved in a mixture of water and diethyl ether and the aqueous layer was separated out. The aqueous solution was adjusted to pH 4 to 5 with 10% hydrochloric acid and the resulting precipitates were collected by filtration, washed with water and dried to give 1-(6-amino-9H-purin-9-yl)-1,3-dideoxy-3-(N-benzyloxycarbonyl-L-phenylalanylamino)-β-D-ribofuranuronic acid (267 mg), mp. 195°–201° C. (dec.).

IR (nujol): 3300, 1690, 1650, 1610, 1530, 1330, 1300, 1255, 1130, 1110, 1080, 1045 cm$^{-1}$.

NMR (CDCl$_3$, δ): 2.67–3.04 (2H, m), 4.29–4.77 (4H, m), 4.91 (2H, m), 6.14 (1H, m), 7.21 (13H, m), 8.15 (1H, s), 8.41 (1H, m), 8.57 (1H, s).

EXAMPLE 24

1-(6-amino-9H-purin-9-yl)-1,3-dideoxy-3-(D,L-3-tert-butoxycarbonylamino-3-phenylpropionylamino)-β-D-ribofuranuronic acid (214 mg) was prepared by reacting 1-(6-benzoylamino-9H-purin-9-yl)-1,3-dideoxy-3-(D,L-3-tert-butoxycarbonylamino-3-phenylpropionylamino)-β-D-ribofuranuronic acid (340 mg) prepared in Example 7 with n-butylamino (3 ml) according to a similar manner to that of Example 23, mp. 198°–203° C. (dec.).

IR (nujol): 3330, 1685, 1650, 1630, 1570, 1525, 1290, 1280, 1245, 1210, 1165, 1085, 1055, 1020 cm$^{-1}$.

NMR (DMSO-d$_6$, δ): 1.35 (9H, s), 2.62 (2H, m), 4.32 (1H, m), 4.46 (2H, m), 5.07 (1H, m), 6.12 (1H, m), 7.30 (8H, s), 8.17 (2H, s), 8.46 (1H, s).

EXAMPLE 25

1-(6-Amino-9H-purin-9-yl)-3-(phenylacetylamino)-1,3-dideoxy-β-D-ribofuranuronic acid (97 mg) was prepared by reacting 1-(6-benzoylamino-9H-purin-9-yl)-3-(phenylacetylamino-1,3-dideoxy-β-D-ribofuranuronic acid (340 mg) prepared in Example 17 with n-butylamine according to a similar manner to that of Example 23, mp. 159°–165° C. (dec.).

IR (nujol): 3350–3150, 1690, 1650, 1600, 1210, 1080 cm$^{-1}$.

NMR (DMSO-d$_6$+D$_2$O, δ): 3.55 (2H, s), 4.2–4.9 (2H, m), 6.1 (1H, m), 7.23 (5H, s), 8.13 (1H, s), 8.42 (1H, s).

EXAMPLE 26

1-(6-Amino-9H-purin-9 yl)-3-(N-tert-butoxycarbonyl-D,L-phenylglycylamino)-1,3-dideoxy-β-D-ribofuranuronic acid (75 mg) was prepared by reacting 1-(6-benzoylamino-9H-purin-9-yl)-3-(N-tert-butoxycarbonyl-D,L-phenylglycylamino)-1,3-dideoxy-β-D-ribofuranuronic acid (270 mg) prepared in Example 8 with n-butylamine (2.6 ml) according to a similar manner to that of Example 23, mp. 175°–182° C. (dec.).

IR (nujol): 3300, 1690–1650, 1165 cm$^{-1}$.

NMR (DMSO-d$_6$+D$_2$O, δ): 1.22 (9H, s), 4.2–4.5 (1H, m), 4.5–4.7 (2H, m), 5.2–5.4 (1H, m), 6.2 (1H, m), 7.1–7.5 (5H, m), 8.17 (1H, s), 8.47 (1H, s).

EXAMPLE 27

1-(6-Amino-9H-purin-9-yl)-3-[N-tert-butoxycarbonyl-β-(4-fluorophenyl)-D,L-alanylamino]-1,3-dideoxy-β-D-ribofuranuronic acid (400 mg) was prepared by reacting 1-(6-benzoylamino-9H-purin-9yl)-3-[N-tert-butoxycarbonyl-β-(4-fluorophenyl)-D,L-alanylamino]-1,3-dideoxy-β-D-ribofuranuronic acid (543 mg) prepared in Example 9 with n-butylamine (5.0 ml) according to a similar manner to that of Example 23, mp. 149°–154° C. (dec.).

IR (nujol): 3300, 1690–1650, 1510, 1220, 1170 cm$^{-1}$.

NMR (DMSO-d$_6$+D$_2$O, δ): 2.7–3.1 (2H, m), 4.0–4.2 (1H, m), 4.2–4.5 (1H, m), 4.5–4.8 (2H, m), 6.1 (1H, m), 6.8–7.4 (4H, m), 8.14 (1H, s), 8.49 (1H, s).

EXAMPLE 28

1-(6-Amino-9H-purin-9-yl)-3-(N-tert-butoxycarbonyl-O-methyl-β-phenyl-D,L-erythro-serylamino)-1,3-dideoxy-β-D-ribofuranuronic acid (200 mg) was prepared by reacting 1-(6-benzoylamino-9H-purin-9yl)-3-(N-tert-butoxycarbonyl-O-methyl-β-phenyl-D,L-erythroserylamino)-1.3-dideoxy-β-D-ribofuranuronic acid (331 mg) prepared in Example 10 with n-butylamine according to a similar manner to that of Example 23 mp 177°–182° C. (dec.).

IR (nujol): 3300, 3200, 1690, 1660, 1170, 1090 cm$^{-1}$.

NMR (DMSO-d$_6$+D$_2$O, δ): 1.22 (9H, s), 3.08 (3H, s), 4.1–4.6 (3H, m), 4.5–4.9 (2H, m), 6.2 (1H, m), 7.31 (5H, s), 8.25 (1H, s), 8.46 (1 H, s).

EXAMPLE 29

1-(6-Amino-9H-purin-9-yl)-3-(N$^α$,N$^ε$-dibenzyloxycarbonyl-L-lysylamino-1,3-dideoxy-β-D-ribofuranuronic acid (250 mg) was prepared by reacting 1-(6-benzoylamino-9H-purin-9-yl)-3-(N$^α$,N$^ε$-dibenzyloxycarbonyl-L-lysylamino)-1,3-dideoxy-β-D-ribofuranuronic acid (390 mg) prepared in Example 11 with n-butylamine according to a similar manner to that of Example 23, mp. 86°–100° C.

NMR (DMSO-d$_6$+D$_2$O, δ): 1.1–1.7 (6H, m), 2.8–3.1 (2H, m), 4.0–4.8 (4H, m), 4.99 (4H, s), 6.1 (1H, s), 7.28 (10H, s), 8.13 (1H, s), 8.45 (1H, s).

IR (nujol): 3300, 1690, 1530, 1250, 1080 cm$^{-1}$.

EXAMPLE 30

1-(6-Amino-9H-purin-9-yl)-3-(N-benzyloxycarbonyl-O-benzyl-L-tyrosylamino)-1,3-dideoxy-β-D-ribofuranuronic acid (130 mg) was prepared by reacting 1-(6-benzoylamino-9H-purin-9-yl)-3-(N-benzyloxycarbonyl-O-benzyl-L-tyrosylamino)-1,3-dideoxy-β-D-ribofuranuronic acid (190 mg) prepared in Example 12 with n-butylamine (1.5 ml) according to a similar manner to that of Example 23, mp. 173°–176° C. (dec.).

IR (nujol): 3300, 1690, 1655, 1540, 1515, 1270, 1230, 1085, 1055 cm$^{-1}$.

NMR (DMSO-d$_6$+D$_2$O, δ): 2.83 (2H, m), 3.9–4.8 (4H, m), 4.91 (2H, s), 5.03 (2H, s), 6.10 (1H, d, J=2 Hz), 6.87 (2H, d, J=8 Hz), 7.22 (5H, s), 7.23 (2H, d, J=8 Hz), 7.34 (5H, s), 8.16 (1H, s), 8.44 (1H, s).

EXAMPLE 31

1-(6-Amino-9H-purin-9-yl)-3-(N-benzyloxycarbonyl-L-alanylamino)-1,3-dideoxy-β-D-ribofuranuronic acid (190 mg) was prepared by reacting 1-(6-benzoylamino-9H-purin-9-yl)-3-(N-benzyloxycarbonyl-L-alanylamino)-1,3-dideoxy-β-D-ribofuranuronic acid (280 mg) prepared in Example 13 with n-butylamine (1.5 ml) according to a similar manner to that of Example 23, mp. 151°–156° C. (dec.).

IR (nujol): 3320, 1690, 1610, 1535, 1260–1230, 1085 cm$^{-1}$.

NMR (DMSO-d$_6$+D$_2$O, δ): 1.23 (3H, d, J=7 Hz), 3.8–4.8 (4H, m), 5.10 (2H, s), 6.17 (1H, d, J=2 Hz), 7.40 (5H, s), 8.27 (1H, s), 8.40 (1H, s).

EXAMPLE 32

1-(6-Amino-9H-purin-9-yl)-3-(N-benzyloxycarbonyl-β-alanylamino-1,3-dideoxy-β-D-ribofuranuronic acid (250 mg) was prepared by reacting 1-(6-benzoylamino-9H-purin-9-yl)-3-(N-benzyloxycarbonyl-β-alanylamino)-1,3-dideoxy-β-D-ribofuranuronic acid (570 mg) prepared in Example 14 with n-butylamine (2ml) according to a similar manner to that of Example 23, mp. 195°–198° C.

IR (nujol): 3350, 3200, 1710, 1690, 1640, 1560, 1535 cm$^{-1}$.

NMR (DMSO-d$_6$+D$_2$O, δ): 2.38 (2H, t, J=7 Hz), 3.23 (2H, t, J=7 Hz), 4.3–4.9 (4H, m), 6.08 (1H, d, J=2 Hz), 7.29 (5H, s), 8.14 (1H, s), 8.48 (1H, s).

EXAMPLE 33

1-(6-Amino-9H-purin-9-yl)-3-(3-phenylpropionylamino)-1,3-dideoxy-β-D-ribofuranuronic acid (89 mg) was prepared by reacting 1-(6-benzoylamino-9H-purin-9-yl)-3-(3-phenylpropionylamino)-1,3-dideoxy-β-D-ribofuranuronic acid (365 mg) prepared in Example 18 with n-butylamine (3 ml) according to a similar manner to that of Example 23, mp. 191°–197° C. (dec.).

IR (nujol): 3400, 3300, 1690, 1650, 1610, 1545, 1535, 1415, 1240, 1220, 1090 cm$^{-1}$.

NMR (DMSO-d$_6$, δ): 2.74 (4H, m), 4.33–5.00 (3H, m), 6.15 (1H, d, J=2 Hz), 7.24 (5H, s), 7.31 (2H, s), 8.18 (1H, s), 8.29 (1H, s), 8.46 (1H, s).

EXAMPLE 34

1-(6-Amino-9H-purin-9-yl)-3-benzoylamino-1,3-dideoxy-β-D-ribofuranuronic acid (75 mg) was prepared by reacting 1-(6-benzoylamino-9H-purin-9-yl)-3-benzoylamino-1,3-dideoxy-β-D-ribofuranuronic acid (200 mg) prepared in Example 19 with n-butylamine (2.5 ml) according to a similar manner to that of Example 23, mp. 237°–239° C. (dec.).

IR (nujol): 3420, 3310, 3210, 3140, 3075, 1715, 1690, 1650, 1610, 1570, 1525, 1290, 1240, 1193, 1170, 1100, 1080 cm$^{-1}$.

NMR (DCl+D$_2$O, δ): 5.15 (3H, m), 6.66 (1H, s), 7.44–7.96 (5H, m), 8.76 (1H, s), 9.72 (1H, s).

EXAMPLE 35

1-(6-Amino-9H-purin-9-yl)-3-D-mandelylamino-1,3-dideoxy-β-D-ribofuranuronic acid (35 mg) was prepared by reacting 1-(6-benzoylamino-9H-purin-9-yl)-3-D-mandelylamino-1,3-dideoxy-β-D-ribofuranuronic acid (370 mg) prepared in Example 22 with n-butylamine (3ml) according to a similar manner to that of Example 23.

IR (nujol): 3700–3000, 1690, 1650, 1600, 1525, 1410, 1300, 1210, 1080, 1060 cm$^{-1}$.

NMR (DMSO-d$_6$, δ): 4.37–4.77 (4H, m), 5.00 (1H, m), 6.09 (1H, d, J=1.5 Hz), 6.23–6.53 (1H, m), 7.32 (7H, m), 8.12 (1H, s), 8.40 (1H, s).

EXAMPLE 36

1-(6-Amino-9H-purin-9-yl)-1,3-dideoxy-3-(N-benzyloxycarbonyl-D-phenylalanylamino)-β-D-ribofuranuronic acid (199 mg) was prepared by reacting 1-(6-benzoylamino-9H-purin-9-yl)-1,3-dideoxy-3-(N-benzyloxycarbonyl-D-phenylalanylamino)-β-D-ribofuranuronic acid (360 mg) prepared in Example 6 with n-butylamine (3 ml) according to a similar manner to that of Example 23, mp. 196°–202° C. (dec.).

IR (nujol): 3280, 1695, 1650, 1535, 1260, 1115, 1085, 1050, 1025 cm$^{-1}$.

NMR (DMSO-d$_6$, δ): 2.70–3.11 (2H, m), 4.33–4.83 (4H, m), 4.94 (2H, s), 6.15 (2H, m), 7.25 (12H, s), 8.16 (1H, s), 8.16–8.45 (1H, m), 8.45 (1H, s).

EXAMPLE 37

1-(6-Amino-9H-purin-9-yl)-3-[N-(N-benzyloxycarbonylglycyl)-O-methyl-L-tyrosylamino]-1,3-dideoxy-β-D-ribofuranuronic acid (242 mg) was prepared by reacting 1-(6-benzoylamino-9H-purin-9-yl)-3-[N-(N-benzyloxycarbonylglycyl)-O-methyl-L-tyrosylamino]-1,3-dideoxy-β-D-ribofuranuronic acid (752 mg) prepared in Example 15 with n-butylamine (4 ml) according to a similar manner to that of Example 23, mp. 118°–125° C. (dec.).

IR (nujol): 3300, 1700, 1680, 1650, 1610, 1245, 1180, 1155, 1110, 1050, 1035 cm$^{-1}$.

NMR (DMSO-d$_6$, δ): 2.80–3.00 (2H, m), 3.56 (2H, m), 3.68 (3H, s), 4.29–4.81 (4H, m), 5.01 (2H, s), 6.11 (2H, m), 6.77 (2H, d), 7.07–7.40 (4H, m), 7.31 (5H, s), 7.91 (1H, m), 8.14 (1H, s), 8.41 (1H, s).

EXAMPLE 38

A mixture of 1-(6-benzoylamino-9H-purin-9-yl)-3-amino-1,3-dideoxy-β-D-ribofuranuronic acid (1.0 g) prepared in Example 1, concentrated aqueous ammonia (16 ml) and methanol (8 ml) was refluxed for 1.75 hours. The reaction mixture was evaporated to dryness and the residue was triturated in methanol (20 ml) to give 1-(6-amino-9H-purin-9-yl)-3-amino-1,3-dideoxy-β-D-ribofuranuronic acid (554 mg), mp. 245°–249° C. (dec.).

IR (nujol): 3550, 3300, 1670, 1610, 1575 cm$^{-1}$.

NMR (D$_2$O+DCl, δ): 5.09 (1H, d, J=7 Hz), 5.17 (1H, dd, J=2 and 6 Hz), 6.40 (1H, d, J=2 Hz), 8.43 (1H, s), 8.52 (1H, s).

EXAMPLE 39

A solution of 1-(6-amino-9H-purin-9-yl)-1,3-dideoxy-3-(N-benzyloxycarbonyl-L-phenylalanylamino)-β-D-ribofuranuronic acid (220 mg) prepared in Example 23 in 65% aqueous ethanol (150 ml) was adjusted to pH 2.5 with 1N hydrochloric acid and hydrogenated at 3 atmospheric pressure for 11 hours at room temperature over 10% palladiumcharcoal (100 mg).

After the catalyst removed by filtration, the filtrate was adjusted to pH 7 with aqueous sodium hydroxide and concentrated to remove ethanol under reduced pressure. The aqueous solution was subjected to column chromatography on a non ionic adsorption resin HP-20 (trade mark, Mitsubishi Chemical Industries Ltd.) (100 ml). After the column was washed with water, the elution was carried out with 30% aqueous methanol. The eluate was evaporated to remove methanol under reduced pressure and lyophilized to give 1-(6-amino-9H-purin-9-yl)-1,3-dideoxy-3-(L-phenylalanylamino)-β-D-ribofuranuronic acid (121 mg), mp. 194°–196° C. (dec.).

IR (nujol): 3300, 3175, 1640, 1600, 1400, 1325, 1300, 1245, 1210, 1170, 1075 cm$^{-1}$.

NMR (DCl+D$_2$O, δ): 3.24 (2H, d), 6.21 (1H, d, J=2 Hz), 7.34 (5H, s), 8.41 (1H, s), 8.58 (1H, s).

EXAMPLE 40

1-(6-Amino-9H-purin-9-yl)-3-(L-lysylamino)-1,3-dideoxy-β-D-ribofuranuronic acid (64 mg) was prepared by hydrogenation of 1-(6-amino-9H-purin-9-yl)-3-(N$^\alpha$,N$^\epsilon$-dibenzyloxycarbonyl-L-lysylamino)-1,3-dideoxy-β-D-ribofuranuronic acid (222 mg) prepared in Example 29 according to a similar manner to that of Example 39, mp. 165°–172° C. (dec.).

IR (nujol): 3300, 3150, 3050, 1640, 1600 cm$^{-1}$.

NMR (DMSO-d$_6$+D$_2$O, δ): 1.1–1.9 (6H, m), 2.5–2.9 (2H, m), 3.3–3.9 (1H, m), 4.1–4.7 (3H, m), 6.0 (1H, m), 8.17 (1H, s), 9.10 (1H, s).

EXAMPLE 41

1-(6-Amino-9H-purin-9-yl)-3-(L-tyrosylamino)-1,3-dideoxy-β-D-ribofuranuronic acid (27 mg) was prepared by hydrogenation of 1-(6-amino-9H-purin-9-yl)-3-(N-benzyloxycarbonyl-O-benzyl-L-tyrosylamino)-1,3-dideoxy-β-D-ribofuranuronic acid (115 mg) prepared in Example 30 according to a similar manner to that of Example 39, mp. 205°–207° C. (dec.).

IR (nujol): 3500–3200, 1690–1670, 1630, 1610, 1520 cm$^{-1}$.

NMR (D$_2$O+DCl, δ): 3.15 (2H, d, J=7 Hz), 4.44 (1H, t, J=7 Hz), 4.72 (1H, m), 4.99 (2H, m), 6.49 (1H, bs), 8.75 (1H, s), 9.74 (1H, s).

EXAMPLE 42

1-(6-Amino-9H-purin-9-yl)-3-(L-alanylamino)-1,3-dideoxy-β-D-ribofuranuronic acid (33 mg) was prepared by hydrogenation of 1-(6-amino-9H-purin-9-yl)-3-(N-benzyloxycarbonyl-L-alanylamino)-1,3-dideoxy-β-D-ribofuranuronic acid (170 mg) prepared in Example 31 according to a similar manner to that of Example 39, mp. 150°–155° C. (dec.).

IR (nujol): 3400–3100, 1650, 1600, 1580, 1560 cm$^{-1}$.

NMR (D$_2$O+DCl, δ): 1.63 (3H, d, J=7 Hz), 4.36 (1H, q, J=7 Hz), 4.7–5.4 (3H, m), 6.49 (1H, d, J=2 Hz), 8.63 (1H, s), 9.22 (1H, s).

EXAMPLE 43

1-(6-Amino-9H-purin-9-yl)- 3-β-alanylamino-1,3-dideoxy-β-D-ribofuranuronic acid (58 mg) was prepared by hydrogenation of 1-(6-amino-9H-purin-9-yl)-3-(N-benzyloxycarbonyl-β-alanylamino)-1,3-dideoxy-β-D-ribofuranuronic acid (215 mg) prepared in Example 32 according to a similar manner to that of Example 39, mp. 202°–205° C. (dec.).

IR (nujol): 3400–3150, 1660, 1640, 1605, 1580, 1550 cm$^{-1}$.

NMR (D$_2$O+DCl, δ): 2.62 (2H, t, J=7 Hz), 3.33 (2H, t, J=7 Hz), 6.34 (1H, d, J=2 Hz), 8.47 (1H, s), 8.67 (1H, s).

EXAMPLE 44

1-(6-Amino-9H-purin-9-yl)-1,3-dideoxy-3-(D-phenylalanylamino)-β-D-ribofuranuronic acid (91 mg) was prepared by hydrogenation of 1-(6-amino-9H-purin-9-yl)-1,3-dideoxy-3-(N-benzyloxycarbonyl-D-phenylalanylamino)-β-D-ribofuranuronic acid (170 mg) prepared in Example 36 according to a similar manner to that of Example 39, mp, 203°–204° C. (dec.).

IR (nujol): 3325, 3175, 1640, 1600, 1330, 1300, 1245, 1210, 1175, 1110, 1075 cm$^{-1}$.

NMR (DCl+D$_2$O, δ): 3.25 (2H, d), 6.25 (1H, m), 7.32 (5H, s), 8.46 (1H, s), 8.61 (1H, s).

EXAMPLE 45

A mixture of 1-(6-amino-9H-purin-9-yl)-1,3-dideoxy-3-(D,L-3-tert-butoxycarbonylamino-3-phenyl propionylamino)-β-D-ribofuranuronic acid (170 mg) prepared in Example 24 and formic acid (2.6 ml) was stirred for 2 hours at room temperature and evaporated to dryness. The residue was dissolved in water (20 ml) and adjusted to pH 7 with aqueous sodium bicarbonate. The solution was subjected to column chromatography on a non ionic adsorption resin "HP-20" (trade mark, Mitsubishi Chemical Industries Ltd.) (85 ml). After the column was washed with water, the elution was carried out with 30% aqueous methanol. The eluate was evaporated to remove methanol under reduced pressure and lyophilized to give 1-(6-amino-9H-purin-9-yl)-1,3-dideoxy-3-(D,L-3-amino-3-phenylpropionylamino)-β-D-ribofuranuronic acid (79 mg), mp. 206°–207° C. (dec.).

IR (nujol): 3700–3000, 1640, 1600, 1415, 1330, 1300, 1240, 1210, 1075 cm$^{-1}$.

NMR (DCl+D$_2$O, δ): 3.19 (2H, d), 6.26 (1H, d), 7.45 (5H, s), 8.42 (1H, s), 8.59 (1H, s).

EXAMPLE 46

1-(6-Amino-9H-purin-9-yl)-3-(D,L-phenyl-glycylamino)-1,3-dideoxy-β-D-ribofuranuronic acid (35 mg) was prepared by reacting 1-(6-amino-9H-purin-9-yl)-3-(N-tert-butoxycarbonyl-D,L-phenylglycylamino)-1,3-dideoxy-β-D-ribofuranuronic acid (54 mg) prepared in Example 26 with formic acid (1 ml) according to a similar manner to that of Example 45, mp. 197°–205° C. (dec.).

IR (nujol): 3300, 3200, 1635, 1595, 1070 cm$^{-1}$.

NMR (DMSO-d$_6$, δ): 4.1–4.7 (3H, m), 4.8 (1H, m), 6.1 (1H, m), 7.1–7.6 (5H, m), 8.10 (1H, s), 8.77 and 8.82 (1H, s).

EXAMPLE 47

1-(6-Amino-9H-purin-9-yl)-3-(O-methyl-β-phenyl-D,L-erythro-serylamino)-1,3-dideoxy-β-D-ribofuranuronic acid (91 mg) was prepared by reacting 1-(6-amino-9H-purin-9-yl)-3-(N-tert-butoxycarbonyl-O-methyl-β-phenyl-D,L-erythro-serylamino)-1,3-dideoxy-β-D-ribofuranuronic acid (170 mg) prepared in Example 28 with formic acid (2.6 ml) according to a similar manner to that of Example 45, mp. 185°–190° C. (dec.).

IR (nujol): 3300, 3170, 1640, 1600, 1090, 1070 cm$^{-1}$.

NMR (DMSO-d$_6$+D$_2$O, δ): 3.13 (3H, s), 3.5 (1H, m), 3.9–4.1 (1H, m), 4.1–4.7 (3H, m), 6.1 (1H, m), 7.27 (5H, s), 8.12 (1H, s), 8.89 (1H, broad s).

EXAMPLE 48

1-(6-Amino-9H-purin-9-yl)-3-[β-(4-fluorophenyl)-D,L-alanylamino]-1,3-dideoxy-β-D-ribofuranuronic acid (173 mg) was prepared by reacting 1-(6-amino-9H-purin-9-yl)-3-[N-tert-butoxycarbonyl-β-(4-fluorophenyl)-D,L-alanylamino]-1,3-dideoxy-β-D-ribofuranuronic acid (320 mg) prepared in Example 27 and formic acid (5 ml) according to a similar manner to that of Example 45, mp. 120°–130° C. (dec.).

IR (nujol): 3300, 3200, 1640, 1600, 1510, 1300, 1220, 1075 cm$^{-1}$.

NMR (DMSO-d$_6$+D$_2$O, δ): 2.7–3.1 (2H, m), 3.6–4.1 (1H, m), 4.1–4.3 (1H, m), 4.3–4.6 (2H, m), 6.1 (1H, m), 6.8–7.5 (4H, m), 8.13 (1H, s), 9.10 (1H, s).

EXAMPLE 49

A mixture of N-(N-benzyloxycarbonyl-β-phenyl-D,L-threo-seryl)-N'-tert-butoxycarbonylhydrazine (515 mg) and trifluoroacetic acid (3.5 ml) was stirred for 50 minutes in an ice bath and evaporated to dryness. The residue was dissolved in N,N-dimethylformamide (3.5 ml), cooled to −20° C. and 0.24 ml of 10N hydrogen chloride in tetrahydrofuran was added thereto. To the mixture was added amylnitrite (152 mg) at −20° C. under stirring, which was continued for 20 minutes at the same temperature. The solution was neutralized with triethylamine (15 drops) at the same temperature and cooled to −30° C. To the activated solution was dropped a solution of 1-(6-benzoylamino-9H-purin-9-yl)-1,3-dideoxy-3-amino-β-D-ribofuranuronic acid (365 mg) prepared in Example 1 and triethylamine (285 mg) in N,N-dimethylformamide (2 ml) at −30° C. and the mixture was stirred for 24 hours at −25° to −20° C. The reaction mixture was diluted with water (15 ml) and adjusted to pH 2 with 1N hydrochloric acid. The resulting precipitates were collected by filtration, washed with water and dried to give 1-(6-benzoylamino-9H-purin-9-yl)-1,3-dideoxy-3-(N-benzyloxycarbonyl-β-phenyl-D,L-threo-serylamino)-β-D-ribofuranuronic acid (570 mg).

IR (nujol): 3350, 1705, 1650, 1610, 1590 cm$^{-1}$.

NMR (DMSO-d$_6$+D$_2$O, δ): 4.3–5.4 (5H, m), 4.91 (2H, bs) 6.34 (1H, bs), 7.30 (10H, bs), 7.4–8.6 (5H, m), 8.77 (1H, bs), 8.87 (1H, bs).

EXAMPLE 50

1-(6-Amino-9H-purin-9-yl)-3-(N-benzyloxycarbonyl-β-phenyl-D,L-threo-serylamino)-1,3-dideoxy-β-D-ribofuranuronic acid (296 mg) was prepared by reacting 1-(6-benzoylamino-9H-purin-9-yl)-1,3-dideoxy-3-(N-benzyloxycarbonyl-β-phenyl-D,L-threo-serylamino)-β-D-ribofuranuronic acid (500 mg) prepared in Example 49 with n-butylamine (4.5 ml) according to a similar manner to that of Example 23, mp. 155°–165° C. (dec.).

IR (nujol): 3400–3100, 1710–1650, 1600, 1220, 1080, 1060 cm$^{-1}$.

NMR (DMSO-d$_6$+D$_2$O, δ): 3.7–4.1 (1H, m), 4.2–4.8 (3H, m), 4.92 (2H, s), 5.08 (1H, d, J=4 Hz), 6.1 (1H, m), 7.1–7.5 (10H, m), 8.13 (1H, s), 8.55 (1H, bs).

EXAMPLE 51

1-(6-Amino-9H-purin-9-yl)-3-(β-phenyl-D,L-threo-serylamino)-1,3-dideoxy-β-D-ribofuranuronic acid (142 mg) was prepared by hydrogenation of 1-(6-amino-9H-purin-9-yl)-3-(N-benzyloxycarbonyl-β-phenyl-D,L-threo-serylamino)-1,3-dideoxy-β-D-ribofuranuronic acid (275 mg) prepared in Example 50 according to a similar manner to that of Example 39, mp. 190°–195° C. (dec.).

IR (nujol): 3300, 3200, 1630, 1330, 1300, 1240, 1205, 1070 cm$^{-1}$.

NMR (DMSO-d$_6$+D$_2$O, δ): 3.7–4.1 (1H, m), 4.1–4.7 (3H, m), 5.1 (1H, m), 6.0 (1H, m), 7.1–7.5 (5H, m), 8.13 (1H, s), 9.02 and 9.07 (1H, s).

EXAMPLE 52

1-(6-Amino-9H-purin-9-yl)-1,3-dideoxy-3-(N-glycyl-O-methyl-L-tyrosylamino)-β-D-ribofuranuronic acid (57 mg) was prepared by hydrogenation of 1-(6-amino-9H-purin-9-yl)-3-[N-(N-benzyloxycarbonylglycyl)-O-methyl-L-tyrosylamino]-1,3-dideoxy-β-D-ribofuranuronic acid (210 mg) prepared in Example 37 according to a similar manner to that of Example 39, mp. 194°–197° C. (dec.).

IR (nujol): 3300, 3180, 1650, 1605, 1510, 1300, 1245, 1210, 1180, 1110, 1080 cm$^{-1}$.

NMR (DMSO-d$_6$+D$_2$O, δ): 2.69–2.99 (2H, m), 3.41 (2H, m), 3.70 (3H, s), 4.16–4.72 (4H, m), 6.09 (1H, m), 6.72–6.88 (2H, m), 7.02–7.24 (2H, m), 8.16 (1H, s), 9.14 (1H, m).

EXAMPLE 53

(1) A mixture of 1-(6-benzoylamino-9H-purin-9-yl)-1,3-dideoxy-3-(N-benzyloxycarbonyl-O-methyl-L-tyrosylamino)-β-D-ribofuranuronic acid (300 mg) prepared in Example 2, N-hydroxysuccinimide (50 mg) and dicyclohexylcarbodiimide (100 mg) in dioxane (5 ml) was stirred for 3 days at room temperature. The resulting precipitate was removed by filtration and the filtrate was evaporated to dryness. The residue was triturated in diethyl ether to give N-hydroxysuccinimide ester of 1-(6-benzoylamino-9H-purin-9-yl)-1,3-dideoxy-3-(N-benzyloxycarbonyl-O-methyl-L-tyrosylamino)-β-D-ribofuranuronic acid (300 mg).

IR (nujol): 3250, 1820, 1785, 1740, 1705, 1615, 1585, 1380, 1300, 1250, 1210, 1070 cm$^{-1}$.

NMR (DMSO-d$_6$, δ): 2.48 (4H, s), 2.88 (2H, m), 3.80 (3H, s), 4.28–4.64 (2H, m), 4.80–5.10 (2H, m), 5.03 (2H, s), 6.16–6.57 (2H, m), 6.95 (2H, m), 7.40 (7H, m), 7.64–7.80 (3H, m), 8.08–8.28 (2H, m), 8.92 (2H, m).

(2) A solution of N-hydroxysuccinimide ester of 1-(6-benzoylamino-9H-purin-9-yl)-1,3-dideoxy-3-(N-benzyloxycarbonyl-O-methyl-L-tyrosylamino)-β-D-ribofuranuronic acid (295 mg) prepared in Example 53 (1) in tetrahydrofuran was added to a solution of glycine (30 mg) and triethylamine (0.085 ml) in water (5 ml). The mixture was stirred for 20 hours at room temperature and concentrated under reduced pressure to remove tetrahydrofuran. The aqueous solution was acidified with 1N hydrochloric acid and extracted with a mixed solvent (chloroform/ethanol=1/1). The extract was dried and evaporated to dryness. The residue was triturated in diethyl ether to give N-carboxymethyl-1-(6-benzoylamino-9H-purin-9-yl)-1,3-dideoxy-3-(N-benzyloxycarbonyl-O-methyl-L-tyrosylamino)-β-D-ribofuranuronamide (244 mg), mp. 122°–130° C. (dec.).

IR (nujol): 3230, 1680, 1610, 1580, 1510, 1295, 1240, 1175, 1105, 1060, 1025 cm$^{-1}$.

NMR (DMSO-d$_6$, δ): 2.98–3.19 (2H, m), 3.79 (3H, s), 3.88 (2H, m), 4.27–4.91 (4H, m), 4.97 (2H, s) 6.35 (1H, m), 6.85 (2H, d, J=8 Hz), 7.32 (7H, m), 7.52–7.71 (3H, m), 8.00–8.20 (2H, m), 8.87 (1H, s), 9.10 (1H, m).

EXAMPLE 54

N-Carboxymethyl-1-(6-amino-9H-purin-9-yl)-1,3-dideoxy-3-(N-benzyloxycarbonyl-O-methyl-L-tyroylamino)-β-D-ribofuranuronamide (128 mg) was prepared by reacting N-carboxymethyl-1-(6-benzoylamino-9H-purin-9-yl)-1,3-dideoxy-3-(N-benzyloxycarbonyl-O-methyl-L-tyrosylamino)-β-D-ribofuranuronamide (210 mg) prepared in Example 53 (2) with n-butylamine (1.5 ml) according to a similar manner to that of Example 23, mp. 153°–156° C. (dec.).

IR (nujol): 3280, 3200, 1700, 1660, 1608, 1535, 1515, 1330, 1315, 1300, 1245, 1175 cm$^{-1}$.

NMR (DMSO-d$_6$, δ): 2.78–2.99 (2H, m), 3.69 (3H, s), 4.00–4.77 (4H, m), 4.91 (2H, s), 6.13 (2H, m), 6.78 (2H, d, J=9 Hz), 7.13–7.36 (7H, m), 8.13 (1H, s), 8.43 (1H, s), 8.3–8.5 (1H, m).

EXAMPLE 55

N-Carboxymethyl-1-(6-amino-9H-purin-9-yl)-1,3-dideoxy-3-(O-methyl-L-tyrosylamino)-β-D-ribofuranuronamide (51 mg) was prepared by hydrogenation of N-carboxymethyl-1-(6-amino-9-H-purin-9-yl)-1,3-dideoxy-3-(N-benzyloxycarbonyl-O-methyl-L-tyrosylamino)-β-D-ribofuranuronamide (110 mg) prepared in Example 54 according to a similar manner to that of Example 39, mp. 194°–196° C. (dec.).

IR (nujol): 3700–3000, 1600, 1640, 1600, 1515, 1330, 1305, 1245 cm$^{-1}$.

NMR (DMSO-d$_6$, δ): 2.80–2.92 (2H, m), 3.59 (2H, s), 3.67 (3H, s), 4.13–4.82 (4H, m), 6.08 (1H, m), 6.83 (2H, d, J=8 Hz), 7.17 (2H, d, J=8 Hz), 7.20 (2H, m), 7.90 (1H, m), 8.13 (1H, s), 8.63 (1H, s).

EXAMPLE 56

To a suspension of 1-(6-benzoylamino-9H-purin-9-yl)-1,3-dideoxy-3-(N-benzyloxycarbonyl-O-methyl-L-tyrosylamino)-β-D-ribofuranuronic acid (695 mg) prepared in Example 2 in ethyl acetate (200 ml) was added excess ethereal solution of diazomethane and the mixture was stirred for 30 minutes at room temperature. The resulting solution was evaporated to dryness and the residue was triturated in diethyl ether to give methyl 1-(6-benzoylamino-9H-purin-9-yl)-1,3-dideoxy-3-(N-benzyloxycarbonyl-O-methyl-L-tyrosylamino)-β-D-ribofuranuronate (700 mg), mp. 124°–128° C. (dec.).

IR (nujol): 3300, 1750, 1675, 1614, 1586, 1515, 1300, 1250, 1180, 1095, 1070, 1031 cm$^{-1}$.

NMR (DMSO-d$_6$, δ): 2.84 (2H, m), 3.68 (3H, s), 3.69 (3H, s), 4.04–4.49 (2H, m), 4.81 (2H, m), 4.90 (2H, s), 6.26 (1H, m), 6.43 (1H, m), 6.77 (2H, d, J=9 Hz), 7.16 (8H, m), 7.46–7.62 (3H, m), 7.93–8.12 (2H, m), 8.29–8.50 (1H, m), 8.71 (2H, s).

EXAMPLE 57

Methyl 1-(6-benzoylamino-9H-purin-9-yl)-1,3-dideoxy-3-(O-methyl-L-tyrosylamino)-β-D-ribofuranuronate (238 mg) was prepared as amorphous powder by hydrogenation of methyl 1-(6-benzoylamino-9H-purin-9-yl)-1,3-dideoxy-3-(N-benzyloxycarbonyl-O-methyl-L-tyrosylamino)-β-D-ribofuranuronate (604 mg) prepared in Example 56 according to a similar manner to that of Example 39.

IR (nujol): 1750, 1675, 1615, 1584, 1515, 1300, 1250, 1180, 1100, 1070, 1035 cm$^{-1}$.

NMR (DMSO-d$_6$+D$_2$O, δ): 3.72 (2H, m), 4.26–4.46 (2H, m), 4.65 (2H, m), 6.18 (2H, m), 6.65–7.21 (4H, m), 7.42–7.59 (3H, m), 7.85–8.16 (2H, m), 8.66 (2H, s).

EXAMPLE 58

A mixture of methyl 1-(6-benzoylamino-9H-purin-9-yl)-1,3-dideoxy-3-(N-benzyloxycarbonyl-O-methyl-L-tyrosylamino)-β-D-ribofuranuronate (300 mg) prepared in Example 56 and 100% hydrazine hydrate (4 ml) in methanol (10 ml) was refluxed for 5 hours and evaporated to dryness. The residue was solidified by adding a small amount of methanol and triturated with diethyl ether to give 1-(6-amino-9H-purin-9-yl)-1,3-dideoxy-3-(N-carbazoyl-O-methyl-L-tyrosylamino)-β-D-ribofuranuronohydrazide (190 mg), mp. 152°–158° C. (dec.).

IR (nujol): 3300, 3200, 1640, 1610, 1560, 1510, 1330, 1300, 1245, 1180 cm$^{-1}$.

NMR (DMSO-d$_6$, δ): 2.79 (2H, m), 3.78 (3H, s), 4.20–4.45 (2H, m), 4.52 (2H, m), 6.12 (1H, m), 6.61 (2H, m), 6.87–6.96 (2H, m), 7.08–7.28 (2H, m), 7.38 (2H, m), 8.32 (1H, s), 8.73 (1H, m).

EXAMPLE 59

1-(6-Amino-9H-purin-9-yl)-1,3-dideoxy-3-(O-methyl-L-tyrosylamino)-β-D-ribofuranuronohydrazide (165 mg) was prepared by reacting methyl 1-(6-benzoylamino-9H-purin-9-yl)-1,3-dideoxy-3-(O-methyl-L-tyrosylamino)-β-D-ribofuranuronate (225 mg) prepared in Example 57 with 100% hydrazine hydrate (4 ml) according to a similar manner to that of Example 58, mp. 131°–140° V. (dec.).

IR (nujol): 3280, 1655, 1605, 1510, 1330, 1295, 1245, 1210, 1170, 1100, 1080, 1025 cm$^{-1}$.

NMR (DMSO-d$_6$, δ): 2.80–3.06 (2H, m), 4.40 (m), 4.60 (m), 6.10 (1H, m), 6.84 (2H, d, J=9 Hz), 7.17 (2H, d, J=9 Hz), 7.32 (1H, m), 8.20 (1H, s), 8.68 (1H, s).

EXAMPLE 60

A mixture of methyl 1-(6-benzoylamino-9H-purin-9-yl)-1,3-dideoxy-3-(N-benzyloxycarbonyl-O-methyl-L-tyrosylamino)-β-D-ribofuranuronate prepared in Example 56 (355 mg), n-butylamine (5 ml) and methanol (5 ml) was refluxed for 9 hours. The mixture was evaporated to dryness and the residue was triturated in diethyl ether to give N-n-butyl-1-(6-amino-9H-purin-9-yl)-1,3-dideoxy-3-(N-n-butylcarbamoyl-O-methyl-L-tyrosylamino)-β-D-ribofuranuronamide (208 mg), mp. 111°–115° C. (dec.).

IR (nujol): 3300, 3200, 3100, 1640, 1560, 1505, 1335, 1300, 1245, 1175, 1105, 1075, 1035 cm$^{-1}$.

NMR (DMSO-d$_6$, δ): 0.85 (6H, m), 1.28 (8H, m), 2.68–2.92 (2H, m), 3.05 (4H, m), 3.68 (3H, s), 4.18–4.55 (4H, m), 5.98 (1H, m), 6.32–6.65 (1H, m), 6.75 (2H, d, J=8 Hz), 7.05 (2H, d, J=8 Hz), 7.25 (1H, s), 7.69 (1H, t), 8.11 (1H, s), 8.24 (1H, m), 8.53 (1H, m).

EXAMPLE 61

Methyl 1-(6-benzoylamino-9H-purin-9-yl)-1,3-dideoxy-3-amino-β-D-ribofuranuronate (544 mg) was prepared by hydrogenation of methyl 1-(6-benzoylamino-9H-purin-9-yl)-3-azido-1,3-dideoxy-β-D-ribofuranuronate (1.0 g) prepared in Preparation 6 according to a similar manner to that of Example 1, mp. 148–153° C. (dec.).

IR (nujol): 3500–3300, 1740, 1695, 1610, 1580, 1510, 1400, 1375, 1325, 1290, 1245, 1220, 1175, 1070, 1025 cm$^{-1}$.

NMR (DMSO-d$_6$, δ): 3.77 (3H, s), 3.90 (1H, t, J=6 Hz), 4.42 (1H, d, J=6 Hz), 4.68 (1H, dd, J=3 and 6 Hz), 6.29 (1H, d, J=3 Hz), 7.52–7.76 (3H, m), 8.00–8.21 (2H, m), 8.77 (1H, s), 8.82 (1H, s).

EXAMPLE 62

A mixture of 1-(6-amino-9H-purin-9yl)-1,3-dideoxy-3-amino-β-D-ribofuranuronic acid monohydrate (1.00 g) prepared in Example 99 in 10% (W/V) methanolic hydrogen chloride solution (200 ml) was stirred for 3 hours at room temperature, and evaporated to dryness. The residue was neutralized with aqueous sodium bicarbonate and the resultant solution was saturated with sodium chloride and extracted with a mixture of chloroform and ethanol (1:1). The extract was evaporated to dryness and the residue was triturated in diethyl ether to given methyl 1-(6-amino-9H-purin-9-yl)-1,3-dideoxy-3-amino-β-D-ribofuranuronate (790 mg), mp. 115°–120° C. (dec.).

IR (nujol): 3550, 3250, 3100, 1750, 1680, 1610 1300, 1220, 1120, 1090, 760, 720 cm$^{-1}$.

NMR (DMSO-d$_6$+D$_2$O, δ): 3.72 (3H, s), 4.2–4.6 (3H, m), 6.1 (1H, m), 8.15 (1H, s), 8.37 (1H, s).

EXAMPLE 63

A mixture of 1-(6amino-9H-purin-9-yl)-1,3-dideoxy-3-amino-β-D-ribofuranuronic acid monohydrate (5.00 g) prepared in Example 99 in 10% (W/V) ethanolic hydrogen chloride solution (1 l) was stirred for 4 hours at room temperature, and evaporated to dryness. The residue was neutralized with aqueous sodium bicarbonate and the resultant solution was saturated with sodium chloride, and extracted with a mixture of chloroform and ethanol (3:2). The extract was evaporated to dryness and the residue was triturated with diethyl ether to give ethyl 1-(6-amino-9H-purin-9-yl)-1,3-dideoxy-3-amino-β-D-ribofuranuronate quantitatively, mp. 179°–182° C.

NMR (DMSO-d$_6$+D$_2$O, δ): 1.27 (3H, t, J=7 Hz), 4.18 (2H, q, J=7 Hz), 4.0–4.7 (3H, m), 6.09 (1H, d, J=4 Hz), 8.15 (1H, s), 8.42 (1H, s).

EXAMPLE 64

A mixture of methyl-1-(6-amino-9H-purin-9-yl)-1,3-dideoxy-3-amino-β-D-ribofuranuronate (294 mg) prepared in Example 62, N-tert-butoxycarbonyl-β-(4-chlorophenyl)-D,L-alanine (300 mg) and N,N'-dicyclohexylcarbodiimide (206 mg) in tetrahydrofuran (15 ml) and water (5 ml) was stirred overnight. The mixture was diluted with water (50 ml) and extracted with ethyl acetate. The extract was washed with water, dried, and evaporated to dryness. The residue was subjected to column chromatography on silica gel. The elution was carried out with a mixed solvent (chloroform/methanol=97/3). The eluate was evaporated to dryness to give methyl 1-(6-amino-9H-purin-9-yl)-1,3-dideoxy-3-[N-tert-butoxycarbonyl-β-(4-chlorophenyl)-D,L-alanylamino]-β-D-ribofuranuronate (203 mg), mp. 120°–125° C.

IR (nujol): 3340, 1750, 1660, 1630, 1580 cm$^{-1}$.

NMR (DMSO-d$_6$+D$_2$O, δ): 1.3 (9H, s), 3.68 (3H, s), 4.0–5.0 (4H, m), 6.2 (1H, m), 7.3 (4H, m), 8.17 (1H, s), 8.40 (1H, s).

EXAMPLE 65

A mixture of methyl 1-(6-amino-9H-purin-9-yl)-1,3-dideoxy-3-[N-tert-butoxycarbonyl-β-(4-chlorophenyl)-D,L-alanylamino]-β-D-ribofuranuronate (150 mg) prepared in Example 64 and anisol (0.3 ml) was stirred in an ice-bath, and trifluoroacetic acid (3 ml) was added. After stirring for 1 hour in an ice-bath, diethyl ether was added to the mixture. The resulting precipitates were collected by filtration, added to 1N sodium hydroxide (3 ml), and stirred for 30 minutes in an ice-bath. The reaction mixture was neutralized with 1N hydrochloric acid, subjected to column chromatography on a nonionic adsorption resin "HP-20" (trade mark, Mitsubishi Chemical Industries Ltd.) (30 ml). After the column was washed with water, the elution was carried out with 50% aqueous methanol. The eluate was evaporated to remove methanol under reduced pressure and lyophilized to give 1-(6-amino-9H-purin-9-yl)-1,3-dideoxy-3-[β-(4-chlorophenyl)-D,L-alanylamino]-β-D-ribofuranuronic acid (82 mg), mp. 170°–178° C. (dec.).

IR (nujol): 3600–2100, 1660, 1640, 1600 cm$^{-1}$.

NMR (DCl+D$_2$O, δ): 3.27 (2H, d, J=8 Hz), 4.3–5.2 (4H, m), 6.23 (1H, d, J=2 Hz), 7.5–7.2 (4H, m), 8.45 (1H, s), 8.63 (1H, s).

EXAMPLE 66

Methyl 1-(6-amino-9H-purin-9-yl)-1,3-dideoxy-3-[N-tert-butoxycarbonyl-β-(3-chlorophenyl)-D,L-alanylamino]-β-D-ribofuranuronate (312 mg) was prepared by reacting methyl 1-(6-amino-9H-purin-9-yl)-1,3-dideoxy-3-amino-β-D-ribofuranuronate (294 mg) prepared in Example 62 with N-tert-butoxycarbonyl-β-(3-chlorophenyl)-D,L-alanine (300 mg) according to a similar manner to that of Example 64, mp. 115°–125° C.

(IR (nujol): 3650–2250, 1740, 1660, 1630, 1610, 1580 cm$^{-1}$.

NMR (DMSO-d$_6$+D$_2$O, δ): 1.40 (9H, s), 2.96 (2H, m), 3.68 (3H, s), 4.0–4.9 (4H, m), 6.1 (1H, m), 7.2–7.4 (4H, m), 8.13 (1H, s), 8.43 (1H, s).

EXAMPLE 67

1-(6-Amino-9H-purin-9-yl)-1,3-dideoxy-3-[β-(3-chlorophenyl)-D,L-alanylamino]-β-D-ribofuranuronic acid (135 mg) was prepared from methyl 1-(6-amino-9H-purin-9-yl)-1,3-dideoxy-3-[N-tert-butoxycarbonyl-β-(3-chlorophenyl)-D,L-alanylamino]-β-D-ribofuranuronate (250 mg) prepared in Example 66 according to a similar manner to that of Example 65, mp. 165°–170° C. (dec.).

IR (nujol): 3650–2000, 1690, 1660, 1640, 1600, 1575 cm$^{-1}$.

NMR (DCl+D$_2$O, δ): 3.25 (2H, d, J=7 Hz), 4.2–5.2 (4H, m), 6.28 (1H, d, J=1 Hz), 7.2–7.5 (4H, m), 8.50 (1H, s), 8.63 (1H, s).

EXAMPLE 68

Ethyl 1-(6amino-9H-purin-9-yl)-1,3-dideoxy-3-[N-tert-butoxycarbonyl-β-(2-chlorophenyl)-D,L-alanylamino]-β-D-ribofuranuronate (320 mg) was prepared by reacting ethyl 1-(6-amino-9H-purin-9-yl)-1,3-dideoxy-3-amino-β-D-ribofuranuronate 294 mg) prepared in Example 63 with N-tert-butoxycarbonyl-β-(2-chlorophenyl)-D,L-alanine (300 mg) according to a similar manner to that of Example 64, mp. 120°–130° C.

IR (nujol): 3650–2200, 1740, 1690, 1660, 1640, 1600 cm$^{-1}$.

NMR (DMSO-d$_6$+D$_2$O, δ): 1.28 (3H, t, J=6 Hz), 1.36 (9H, s), 2.93 (2H, m), 3.9–5.0 (6H, m), 6.1 (1H, m), 7.1–7.4 (4H, bs), 8.15 (1H, s), 8.42 (1H, s).

EXAMPLE 69

1-(6Amino-9H-purin-9-yl)-1,3-dideoxy-3-[β-(2-chlorophenyl)-D,L-alanyamino]-β-D-ribofuranuronic acid (155 mg) was prepared from ethyl 1-(6-amino-9H-purin-9-yl)-1,3-dideoxy-3-[N-tert-butoxycarbonyl-β-(2-chlorophenyl)-D,L-alanylamino]-β-D-ribofuranuronate (250 mg) prepared in Example 68 according to a similar manner to that of Example 65, mp. 160°–170° C. (dec.).

IR (nujol): 3650–2300, 1690, 1660, 1640, 1600 cm$^{-1}$.

NMR (DCl+D$_2$O, δ): 3.29 (2H, d, J=7 Hz), 4.3–5.3 (4H, m), 6.3 (1H, m), 7.4 (4H, m), 8.52 (1H, s), 8.67 (1H, s).

EXAMPLE 70

Ethyl 1-(6-amino-9H-purin-9-yl)-1,3-dideoxy-3-[N-tert-butoxycarbonyl-β-(4-tert-butoxycarbonylaminophenyl)-D,L-alanylamino]-β-D-ribofuranuronate (380 mg) was prepared by reacting ethyl 1-(6-amino-9H-purin-9-yl)-1,3-dideoxy-3-amino-β-D-ribofuranuronate (308 mg) prepared in Example 63 with N-tert-butoxycarbonyl-β-(4-tert-butoxycarbonylaminophenyl)-D,L-alanine (380 mg) according to a similar manner to that of Example 64, mp. 160°–170° C. (dec.).

IR (nujol): 3700–2250, 1740, 1690, 1660, 1605, 1580 cm$^{-1}$.

NMR (DMSO-d$_6$+D$_2$O, δ): 1.20 (3H, t, J=7 Hz), 1.30 (9H, s), 1.48 (9H, s), 2.87 (2H, m), 4.0–5.0 (6H, m), 6.2 (1H, m), 7.1–7.5 (4H, m), 8.17 (1H, s), 8.43 (1H, s).

EXAMPLE 71

1-(6-Amino-9H-purin-9-yl)-1,3-dideoxy-3-[β-(4-aminophenyl)-D,L-alanylamino]-β-D-ribofuranuronic acid (103 mg) was prepared from ethyl 1-(6-amino-9H-purin-9-yl)-1,3-dideoxy-3-[N-tert-butoxycarbonyl-β-(4-tert-butoxycarbonylaminophenyl)-D,L-alanylamino]-β-D-ribofuranuronate (250 mg) prepared in Example 70 according to a similar manner to that of Example 65, mp. 180°–190° C. (dec.).

IR (nujol): 3650–2000, 1690, 1660, 1640, 1605, 1580 cm$^{-1}$.

NMR (DCl+D$_2$O, δ): 3.38 (2H, d, J=7 Hz), 4.3–5.4 (4H, m), 6.33 (1H, d, J=2 Hz), 7.5 (4H, m), 8.50 (1H, s), 8.63 (1H, s).

EXAMPLE 72

Ethyl 1-(6-amino-9H-purin-9-yl)-1,3-dideoxy-3-[N-tert-butoxycarbonyl-β-(4-nitrophenyl)-D,L-alanylamino]-β-D-ribofuranuronate (280 mg) was prepared by reacting ethyl 1-(6-amino-9H-purin-9-yl)-1,3-dideoxy-3-amino-β-D-ribofuranuronate (308 mg) prepared in Example 63 with N-tert-butoxycarbonyl-β-(4-nitrophenyl)-D,L-alanine (310 mg) according to a similar manner to that of Example 64, mp. 170°–180° C. (dec.).

IR (nujol): 3650–2250, 1740, 1685, 1675, 1660, 1605, 1570 cm$^{-1}$.

NMR (DMSO-d$_6$+D$_2$O, δ): 1.18 (3H, t, J=7 Hz), 1.27 (9H, s), 3.10 (2H, d, J=7 Hz), 3.9–5.0 (6 H, m), 6.13 (1H, bs), 7.60 (2H, d, J=8 Hz), 8.15 (2H, d, J=8 Hz), 8.17 (1H, s), 8.43 (1H, s).

EXAMPLE 73

1-(6-Amino-9H-purin-9-yl)-1,3-dideoxy-3-[β-(4-nitrophenyl)-D,L-alanylamino]-β-D-ribofuranuronic acid (75 mg) was prepared from ethyl 1-(6-amino-9H-purin-9-yl)-1,3-dideoxy-3-[N-tert-butoxycarbonyl-β-(4-nitrophenyl)-D,L-alanylamino]-β-D-ribofuranuronate (210 mg) prepared in Example 72 according to a similar manner to that of Example 65, mp. 195°–205° (dec.).

IR (nujol): 3650–2250, 1690, 1660, 1640, 1600, 1575 cm$^{-1}$.

NMR (DCl-D$_2$O, δ): 3.45 (2H, d, J=7 Hz), 4.3–5.2 (4H, m), 6.20 (1H, d, J=2 Hz), 7.58 (2H, d, J=8 Hz), 8.28 (2H, d, J=8 Hz), 8.50 (1H, s), 8.63 (1H, s).

EXAMPLE 74

Ethyl 1-(6-amino-9H-purin-9-yl)-1,3-dideoxy-3-[N-tert-butoxycarbonyl-O-(3-tert-butoxycarbonylaminopropyl)-L-tyrosylamino]-β-D-ribofuranuronate (770 mg) was prepared by reacting ethyl 1-(6-amino-9H-purin-9-yl)-1,3-dideoxy-3-amino-β-D-ribofuranuronate (462 mg) prepared in Example 63 with N-tert-butoxycarbonyl-O-(3-tert-butoxycarbonylaminopropyl)-L-tyrosine (906 mg) prepared in Preparation 7 (4) according to a similar manner to that of Example 64, mp. 125°–131° C. (dec.).

IR (nujol): 3310, 3120, 1740, 1680, 1660, 1625, 1575, 1510 cm$^{-1}$.

NMR (DMSO-d$_6$+D$_2$O, δ): 1.19 (3H, t, J=7 Hz), 1.30 (9H, s), 1.40 (9H, s), 1.4–2.1 (2H, m), 2.7–3.4 (4H, m), 3.8–4.5 (7H, m), 4.70 (1H, m), 6.13 (1H, bs), 6.80 (2H, d, J=8 Hz), 7.23 (2H, d, J=8 Hz), 8.13 (1H, s), 8.43 (1H, s).

EXAMPLE 75

1-(6-Amino-9H-purin-9-yl)-1,3-dideoxy-3-[O-(3-aminopropyl)-L-tyrosylamino]-β-D-ribofuranuronic acid (35 mg) was prepared from ethyl 1-(6-amino-9H-purin-9-yl)-1,3-dideoxy-3-[N-tert-butoxycarbonyl-O-(3-tert-butoxycarbonylaminopropyl)-L-tyrosylamino]-β-D-ribofuranuronate (715 mg) prepared in Example 74 according to a smilar manner to that of Example 77, mp. 150°–160° C. (dec.).

IR (nujol): 3600–2250, 1680–1540, 1510 cm$^{-1}$.

NMR (DMSO-d$_6$+D$_2$O, δ): 2.0 (2H, m), 2.8–3.1 (4H, m), 3.7 (1H, m), 3.9–4.7 (6H, m), 6.05 (1H, m), 6.80 (2H, d, J=8 Hz), 7.30 (2H, d, J=8 Hz), 8.15 (1H, s), 9.03 (1H, s).

EXAMPLE 76

Methyl 1-(6-amino-9H-purin-9-yl)-3-[N-tert-butoxycarbonyl-O-methoxycarbonylmethyl-L-tyrosylamino]-1,3-dideoxy-β-D-ribofuranuronate (220 mg) was prepared by reacting methyl 1-(6-amino-9H-purin-9-yl)-3-amino-1,3-dideoxy-β-D-ribofuranuronate (577 mg) prepared in Example 62 with N-tert-butoxycarbonyl-O-methoxycarbonylmethyl-L-tyrosine (520 mg) prepared in Preparation 8 (2) according to a similar manner to that of Example 64, mp. 115°–120° (dec.).

IR (nujol): 3300, 3150, 1740, 1670, 1610, 1510, 1290, 1170, 1090 cm$^{-1}$.

NMR (DMSO-d$_6$+D$_2$O, δ): 1.30 (9H, s), 2.8–3.1 (2H, m), 3.68 (6H, s), 4.0–4.8 (4H, m), 4.75 (2H, s), 6.2 (1H, m), 6.89 (2H, d, J=8 Hz), 7.18 (2H, d, J=8 Hz), 8.23 (1H, s), 8.49 (1H, s).

EXAMPLE 77

A mixture of methyl 1-(6-amino-9H-purin-9-yl)-3-(N-tert-butoxycarbonyl-O-methoxycarbonylmethyl-L-tyroylamino)-1,3-dideoxy-β-D-ribofuranuronate (200 mg) prepared in Example 76 and formic acid (3 ml) was stirred for 3 hours at room temperature and evaporated to dryness. To the residue was added 1N aqueous sodium hydroxide to adjust the resulting solution to pH 7 and a further 1N aqueous sodium hydroxide (3 ml) was added thereto. The mixture was stirred for 15 minutes at room temperature and adjusted to pH 2 with 1N hydrochloric acid. The resulting precipitates were filtered, washed with water and dried to give 1-(6-amino-9H-purin-9-yl)-3-(O-carboxymethyl-L-tyrosylamino)-1,3-dideoxy-β-D-ribofuranuronic acid (125 mg), mp. 209°–212° C. (dec.).

IR (nujol): 3400–3000, 1700–1560, 1510, 1400, 1220, 1060, 730 cm$^{-1}$.

NMR (DMSO-d$_6$+D$_2$O, δ): 2.7–3.2 (2H, m), 3.8–4.2 (1H, m), 4.1–4.7 (5H, m), 6.1 (1H, m), 6.82 (2H, d, J=8 Hz), 7.23 (2H, d, J=8 Hz), 8.20 (1H, s), 8.83 (1H, s).

EXAMPLE 78

Methyl 1-(6-amino-9H-purin-9-yl)-3-tribenzyloxycarbonyl-L-arginylamino-1,3-dideoxy-β-D-ribofuranuronate (535 mg) was prepared by reacting methyl 1-(6-amino-9H-purin-9-yl)-3-amino-1,3-dideoxy-β-D-ribofuranuronate (300 mg) prepared in Example 62 with tribenzyloxycarbonyl-L-arginine (535 mg) according to a similar manner to that of Example 64, mp. 156°–159° C. (dec.).

IR (nujol): 3370, 1749, 1717, 1675, 1643, 1622, 1571, 1532, 1500, 1326, 1305, 1253, 1235, 1095, 1045, 998, 903, 890, 752, 695 cm$^{-1}$.

NMR (DMSO-d$_6$+D$_2$O, δ): 1.65 (4H, m), 3.58 (3H, s), 3.70–4.94 (6H, m), 5.04 (2H, s), 5.08 (2H, s), 5.27 (2H, s), 6.17 (1H, m), 7.37 (15H, s), 8.31 (1H, s), 8.48 (1H, s).

EXAMPLE 79

1-(6-Amino-9H-purin-9-yl)-3-L-arginylamino-1,3-dideoxy-β-D-ribofuranuronic acid (63 mg) was prepared from methyl 1-(6-amino-9H-purin-9-yl)-3-tribenzyloxycarbonyl-L-arginylamino-1,3-dideoxy-β-D-ribofuranuronate (475 mg) prepared in Example 78 according to a similar manner to that of Example 82, mp. 215°–219° (dec.).

IR (nujol): 3300, 3170, 1685–1580, 1410, 1330, 1300, 1246, 1205, 1170, 1072, 1053, 955, 823, 796, 720 cm$^{-1}$.

NMR (DMSO-d$_6$+D$_2$O, δ): 1.71 (4H, m), 3,18 (2H, m), 3.67–4.57 (4H, m), 6.09 (1H, m), 8.19 (2H, m).

EXAMPLE 80

A mixture of 1-(6amino-9H-purin-9-yl)-1,3-dideoxy-3-(O-methyl-L-tyrosylamino)-β-D-ribofuranuronic acid dihydrochloride monohydrate (200 mg) prepared in Example 4 in 5% (W/V) ethanolic hydrogen chloride solution (20 ml) was stirred for 2 hours at room temperature. The resulting precipitates were collected, washed with diethyl ether, and dried to give ethyl 1-(6-amino-9H-purin-9-yl)-1,3,-dideoxy-3-(O-methyl-L-tyrosylamino)-β-D-ribofuranuronate dihydrochloride (110 mg), mp. 198°–204° C. (dec.).

IR (nujol): 3600–2050, 1720, 1700, 1690, 1615 cm$^{-1}$.

NMR (D$_2$O, δ): 1.26 (3H, t, J=7 Hz), 3.20 (2H, d, J=8 Hz), 3.80 (3H, s), 4.10–5.03 (6H, m), 6.15 (1H, d, J=2 Hz), 6.97 (2H, d, J=8 Hz), 7.27 (2H, d, J=8 Hz), 8.30 (1H, s), 8.50 (1H, s).

EXAMPLE 81

A mixture of ethyl 1-(6-amino-9H-purin-9-yl)-1,3-dideoxy-3-(O-methyl-L-tyrosylamino)-β-D-ribofuranuronate dihydrochloride (300 mg) prepared in Example 80 and triethylamine (0.15 ml) in tetrahydrofuran (10 ml) and water (5 ml) was stirred in an ice-bath. To the mixture were added (tribenzyloxycarbonyl-L-arginine (567 mg) and N,N'-dicyclohexylcarbodiimide (242 mg) successively, and the mixture was stirred for one day at room temperature. The resulting precipitates were filtered off, and the filtrate was concentrated. Ethyl acetate was added to the residue and the resulting precipitates were collected, washed with water and ethyl acetate and then dried to give ethyl 1-(6-amino-9H-purin-9yl)-3-[N-(tribenzyloxycarbonyl-L-arginyl)-O-methyl-L-tyrosylamino]-1,3-dideoxy-β-D-ribofuranuronate (287 mg), mp. 173°–177° C. (dec.).

IR (nujol): 3320, 1720, 1685, 1646, 1623, 1572, 1533, 1505, 1290, 1253, 1240, 1222, 1187, 1173, 1097, 1050, 1025, 1005, 970, 907, 890, 810, 805, 774, 695, 638 cm$^{-1}$.

NMR (DMSO-d$_6$+D$_2$O, δ): 1.19 (3H, t, J=7 Hz), 1.55 (4H, m), 3.66 (3H, s), 3.66–4.17 (4H, m), 4.16 (2H, q, J=7 Hz), 4.45–4.82 (2H, m), 5.00 (2H, s), 5.04 (2H, s), 5.19 (2H, s), 6.11 (1H, d, J=2 Hz), 6.73 (2H, d, J=9 Hz), 7.17 (2H, d, J=9 Hz), 7.28 (5H, s), 7.34 (10H, s), 8.14 (1H, s), 8.42 (1H, s).

EXAMPLE 82

To a solution of ethyl 1-(6-amino-9H-purin-9yl)-1,3-dideoxy-3-[N-(tribenzyloxycarbonyl-L-arginyl)-O-methyl-L-tyrosylamino]-β-D-ribofuranuronate (250 mg) prepared in Example 81 in tetrahydrofuran (10 ml) was added 0.1N sodium hydroxide (10 ml), and the mixture was stirred for 1 hour at room temperature. The resulting solution was adjusted to pH 3 with 1N hydrochloric acid and hydrogenated at three atmospheric pressure over 10% palladium-charcoal (250 mg) for 2.5 hours at room temperature. After the catalyst was removed by filteration, the filtrate was neutralized with 1N sodium hydroxide and concentrated to remove tetrahydrofuran under reduced pressure. After filtration, the filtrate was subjected to column chromatography on a non-ionic adsorption resin "HP-20" (trade mark, Mitsubishi Chemical Industries, Ltd.) (80 ml). After the column was washed with water, the elution was carried out with 30% aqueous methanol. The eluate was evaporated to remove methanol under reduced pressure and lyophilized to give 1-(6-amino-9H-purin-9-yl)-1,3-dideoxy-3-[N-(L-arginyl)-O-methyl-L-tyrosylamino]-

β-D-ribofuranuronic acid (54 mg), mp. 194°–200° C. (dec.).

IR (nujol): 3330, 3180, 1640, 1600, 1515, 1330, 1300, 1244, 1176, 1075, 1028 cm$^{-1}$.

NMR (DMSO-d$_6$+D$_2$), δ): 1.58 (4H, m), 3.01 (5H, m) 4.00–4.55 (4H, m), 6.03 (1H, m), 6.79 (2H, d, J=8 Hz), 7.16 (2H, d, J=8 Hz), 8.17 (1H, s), 8.97 (1H, s).

EXAMPLE 83

Methyl 1-(6-amino-9H-purin-9yl)-1,3-dideoxy-3-(O-methyl-L-tyrosylamino)-β-D-ribofuranuronate dihydrochloride (31 mg) was prepared by esterification of 1-(6-amino-9H-purin-9-yl)-1,3-dideoxy-3-(O-methyl-L-tyrosylamine)-β-D-ribofuranuronic acid dihydrochloride monohydrate (54.8 mg) prepared in Example 4 in 5% (W/V) methanoic hydrogen chloride solution (50 ml) according to a similar manner to that of Example 80, mp. 185°–193° C. (dec.).

IR (nujol): 3600–2100, 1735, 1720, 1690, 1660 cm$^{-1}$.

NMR (D$_2$O, δ): 3.20 (2H, d, J=8 Hz), 3.80 (6H, s), 4.2–5.1 (4H, m), 6.13 (1H, d, J=2 Hz), 6.93 (2H, d, J=8 Hz), 7.25 (2H, d, J=8 Hz), 8.33 (1H, s), 8.50 (1H, s).

EXAMPLE 84

1-(6-Amino-9H-purin-9-yl)-3-[N-(N-tert-butoxycarbonyl-β-phenyl-D-alanyl)-O-methyl-L-tyrosylamino]-1,3-dideoxy-β-D-ribofuranuronic acid (488 mg) was prepared by reacting 1-(6-amino-9H-purin-9-yl)-1,3-dideoxy-3-(O-methyl-L-tyrosylamino)-β-D-ribofuranuronic acid dihydrochloride monohydrate (424 mg) prepared in Example 4 with N-hydroxysuccinimide ester of N-tert-butoxycarbonyl-β-phenyl-D-alanine (290 mg) according to a similar manner to that of Example 5, mp. 164°–168° C. (dec.).

IR (nujol): 3300, 1720–1620, 1510, 1240, 1170 cm$^{-1}$.

NMR (DMSO-d$_6$+$_2$O, δ): 1.23 (9H, s), 2.8–3.2 (4H, m), 3.67 (3H, s), 3.9–4.3 (2H, m), 4.3–4.9 (3H, m), 6.2 (1H, m), 6.80 (2H, d, J=8 Hz), 7.17 (5H, s), 7.18 (2H, d, J=8 Hz), 8.30 (1H, s), 8.59 (1H, s).

EXAMPLE 85

1-(6-Amino-9H-purin-9-yl)-1,3-dideoxy-3-[N-(β-phenyl-D-alanyl)-O-methyl-L-tyrosylamino]-β-D-ribofuranuronic acid (240 mg) was prepared by reacting 1-(6-amino-9H-purin-9-yl)-3-[N-(N-tert-butoxycarbonyl-β-phenyl-D-alanyl-O-methyl-L-tyrosylamino]-1,3-dideoxy-β-D-ribofuranuronic acid (420 mg) prepared in Example 84 with formic acid (6.7 ml) according to a similar manner to that of Example 45, mp. 175°–182° C. (dec.).

IR (nujol): 3250, 3150, 1650, 1600, 1510, 1250, 1080, 700 cm$^{-1}$.

NMR (DMSO-d$_6$+D$_2$O, δ): 2.5–3.2 (4H, m), 3.67 (3H, s), 4.1–4.8 (5H, m), 6.1 (1H, m), 6.80 (2H, d, J=8 Hz), 7.17 (5H, s), 7.18 (2H, d, J=8 Hz), 8.18 (1H, s), 9.03 (1H, s).

EXAMPLE 86

1-(6-Amino-9H-purin-9-yl)-3-[N-(N-tert-butoxycarbonyl-O-methyl-L-tyrosyl)-O-methyl-L-tyrosylamino]-1,3-dideoxy-β-D-ribofuranuronic acid (125 mg) was prepared by reacting 1-(6-amino-9H-purin-9-yl)-1,3-dideoxy-3-(O-methyl-L-tyrosylamino)-β-D-ribofuranuronic acid dihydrochloride monohydrate (330 mg) prepared in Example 4 with N-hydroxysuccinimide ester of N-tert-butoxycarbonyl-O-methyl-L-tyrosine (255 mg) according to a similar manner to that of Example 5, mp. 178°–180° C. (dec.).

IR (nujol): 3250, 1720–1630, 1510, 1240, 1170, 1110, 1080, 1030, 820, 720, 640 cm$^{-1}$.

NMR (DMSO-d$_6$+D$_2$O, δ): 1.30 (9H, s), 2.6–3.3 (4H, m), 3.73 (6H, s), 4.0–4.9 (5H, m), 6.3 (1H, m), 6.82 (2H, d, J=8 Hz), 6.87 (2H, d, J=8 Hz), 7.13 (2H, d, J=8 Hz), 7.30 (2H, d, J=8 Hz), 8.45 (1H, s), 8.72 (1H, s).

EXAMPLE 87

1-(6-Amino-9H-purin-9-yl)-3-[N-(O-methyl-L-tyrosyl)-O-methyl-L-tyrosylamino]-1,3-dideoxy-β-D-ribofuranuronic acid (46 mg) was prepared by reacting 1-(6-amino-9H-purin-9-yl)-3-[N-(N-tert-butoxycarbonyl-O-methyl-L-tyrosyl)-O-methyl-L-tyrosylamino]-1,3-dideoxy-β-D-ribofuranuronic acid (100 mg) prepared in Example 86 with formic acid according to a similar manner to that of Example 45, mp. 175°–177° C. (dec.).

IR (nujol): 3400–3100, 1640, 1610, 1510, 1300, 1250, 1180, 1080, 1030 cm$^{-1}$.

NMR (DMSO-d$_6$+D$_2$O, δ): 2.7–3.1 (4H, m), 3.72 (6H, s), 4.0–4.8 (5H, m), 6.2 (1H, m), 6.82 (4H, d, J=8 Hz), 7.12 (2H, d, J=8 Hz), 7.20 (2H, d, J=8 Hz), 8.20 (1H, s), 9.10 (1H, s).

EXAMPLE 88

1-(6-Amino-9H-purin-9-yl)-1,3-dideoxy-3-(L-2-tert-butoxycarbonylamino-4-benzyloxycarbonyl-butyrylamino)-β-D-ribofuranuronic acid (283 mg) was prepared reacting 1-(6-amino-9H-purin-9-yl)-1,3-dideoxy-3-amino-β-D-ribofuranuronic acid monohydrate (298 mg) prepared in Example 99 with N-hydroxysuccinimide ester of L-2-tert-butoxycarbonylamino-4-benzyloxycarbonylbutyric acid (543 mg) according to a similar manner to that of Example 5, mp. 145°–150° C. (dec.).

IR (nujol): 3650–2250, 1730, 1690, 1650, 1610 cm$^{-1}$.

NMR (DMSO-d$_6$+D$_2$O, δ): 1.40 (9H, s), 1.7–2.2 (2H, m), 2.2–2.8 (2H, m), 4.0–5.0 (4H, m), 5.16 (2H, s), 6.18 (1H, d, J=2 Hz), 7.40 (5H, s), 8.33 (1H, s), 8.63 (1H, s).

EXAMPLE 89

A mixture of 1-(6-amino-9H-purin-9-yl)-1,3-dideoxy-3-(L-2-tert-butoxycarbonylamino-4-benzyloxycarbonylbutyrylamino)-β-D-ribofuranuronic acid (200 mg) prepared in Example 88 and anisole (0.5 ml) in trifluoroacetic acid (3 ml) was stirred for one hour in an ice-bath. To the mixture was added diethyl ether (20 ml) and the resulting precipitate was collected by filtration to give ditrifluoroacetic acid salt of 1-(6-amino-9H-purin-9-yl)-1,3-dideooxy-3-(L-2-amino-4-benzyloxycarbonyl-butyrylamino)-β-D-ribofuranuronic acid (192 mg), mp. 120°–130° C. (dec.).

IR (nujol): 3650–2250, 1720, 1695, 1685 cm$^{-1}$.

NMR (D$_2$O, δ): 2.36 (2H, t, J=7 Hz), 2.67 (2H, m), 4.0–5.2 (4H, m), 5.20 (2H, s), 6.30 (1H, d, J=2 Hz), 7.43 (5H, s), 8.43 (1H, s), 8.70 (1H, s).

EXAMPLE 90

A solution of ditrifluoroacetic acid salt of 1-(6-amino-9H-purin-9-yl)-3-(L-2-amino-4benzyloxycarbonyl-butyrylamino)-1,3-dideoxy-β-D-ribofuranuroic acid (140 mg) prepared in Example 89 in water (20 ml) was hydrogenated at atmospheric pressure over palladium black (50 mg) at room temperature. After filtration, the filtrate was adjusted to pH 7 with 1N aqueous sodium hydroxide and subjected to column chromatography on a non ionic adsorption resin "HP-20" (40 ml) (trade mark, Mitsubishi Chemical Industries Ltd.). After the column was washed with water, the elution was carried out with 50% aqueous methanol. The eluant was evaporated to dryness to give 1-(6-amino-9H-purin-9-yl)-1,3-dideoxy-3-(α-L-glutamylamino)-β-D-ribofuranuronic acid (63 mg), mp. 140°-145° C. (dec.).

IR (nujol): 3700-2200, 1660 cm⁻¹.

NMR (D₂O, δ): 2.32 (2H, t, J=7 Hz), 2.6 (2H, m), 4.1-5.2 (4H, m), 6.3 (1H, d, J=2 Hz), 8.43 (1H, s), 8.70 (1H, s).

EXAMPLE 91

A solution of 1-(6-amino-9H-purin-9-yl)-1,3-dideoxy-3-(O-methyl-L-tyrosylamino)-β-D-ribofuranuronic acid dihydrochloride monohydrate (110 mg) prepared in Example 4 in water (100 ml) was adjusted to pH 8.5 with 1N sodium hydroxide and di-tert-butyl dicarbonate (50 mg) was added. The mixture was stirred for 3 hours at room temperature while the medium was adjusted to pH 8.0 to 8.5. The reaction mixture was washed with diethyl ether, adjusted to pH 3 and extracted with a mixed solvent (ethanol/chloroform=1/1). The extract was washed with water, dried, and evaporated to dryness to give 1-(6-amino-9H-purin-9-yl)-1,3-dideoxy-3-(N-tert-butoxycarbonyl-O-methyl-L-tyrosylamino)-β-D-ribofuranuronic acid (108 mg), mp. 179°-186° C. (dec.).

IR (nujol): 3650-2250, 1685, 1660, 1615 cm⁻¹.

NMR (DMSO-d₆+D₂O, δ): 1.30 (9H, s), 2.84 (2H, m), 3.33 (3H, s), 4.0-5.0 (4H, m), 6.24 (1H, d, J=2 Hz), 7.93 (2H, d, J=8 Hz), 7.33 (2H, d, J=8 Hz), 8.24 (1H, s), 8.60 (1H, s).

EXAMPLE 92

A mixture of 1-(6-amino-9H-purin-9-yl)-1,3-dideoxy-3-(N-tert-butoxycarbonyl-O-methyl-L-tyrosylamino)-β-D-ribofuranuronic acid (279 mg) prepared in Example 91, benzyl ester of β-phenyl-D,L-alanine (255 mg), N,N'-dicyclohexylcarbodiimide (124 mg) and N-hydroxysuccinimide (70 mg) in methylene chloride (100 ml) was stirred overnight at room temperature. The resulting precipitates were filtered off, the filtrate was evaporated to dryness. The residue was subjected to column chromatography on silica gel. The elution was carried out with chloroform. The eluate was evaporated to dryness to give benzyl ester on N-[1-(6-amino-9H-purin-9-yl)-1,3-dideoxy-3-(N-tert-butoxycarbonyl-O-methyl-L-tyrosylamino)-β-D-ribofuranuronoyl]-β-phenyl-D,L-alanine (262 mg), mp. 152°-158° C.

IR (nujol): 3700-2300, 1740, 1680, 1640, 1610 cm⁻¹.

NMR (CDCL₃+D₂O, δ): 1.40 (9H, s), 2.8-3.3 (4H, m), 3.70 (3H, s), 4.3-5.1 (5H, m), 5.10 (2H, s), 5.8 (1H, m), 6.75 (2H, d, J=8 Hz), 6.9-7.5 (12H, m), 7.90 (1H, s), 7.93 (1H, s).

EXAMPLE 93

A mixture of benzyl ester of N-[1-(6-amino-9H-purin-9-yl)-1,3-dideoxy-3-(N-tert-butoxycarbonyl-O-methyl-L-tyrosylamino)-β-D-ribofuranuronoyl]-β-phenyl-D,L-alanine (200 mg) prepared in Example 92 and anisole (0.5 ml) was stirred in a ice-bath and trifluoroacetic acid (2 ml) was added to the mixture. After the mixture was stirred for 1 hour in an ice-bath, diethyl ether was added. The resulting precipitates were collected and dried to give ditrifluoroacetate of benzyl ester of N-[1(6-amino-9H-purin-9-yl)-1,3-dideoxy-3-(O-methyl-L-tyrosylamino)-β-D-ribofuranuronoyl]-β-phenyl-D,L-alanine (190 mg), mp. 184°-194° C. (dec.).

IR (nujol): 3650-2250, 1740, 1670 cm⁻¹.

NMR (D₂O+DCl, δ): 2.9-3.6 (4H, m), 3.75 (3H, s), 4.1-5.3 (7H, m), 6.2 (1H, m), 6.7-7.5 (14H, m), 7.83 (1H, s), 8.50 (1H, s).

EXAMPLE 94

A suspension of ditrifluoroacetate of benzyl ester of N-[1-(6-amino-9H-purin-9-yl)-1,3-dideoxy-3-(O-methyl-L-tyrosylamino)-β-D-ribofuranuronoyl]-β-phenyl-D,L-alanine (150 mg) prepared in Example 93 in water (50 ml) was adjusted to pH 3 with 1N hydrochloric acid, and the mixture was hydrogenated over palladium-black (50 mg) at atmospheric pressure. After the reaction was completed, the catalyst was filtered off. The filtrate was adjusted to pH 7 with 1N sodium hydroxide and subjected to column chromatography on a non-ionic adsorption resin "HP-20" (trade mark, Mitsubishi Chemical Industries Ltd.) (50 ml). After the column was washed with water, the elution was carried out with 50% aqueous methanol. The eluate was concentrated under reduced pressure. The resulting precipitates were collected and dried to give N-[1-(6-amino-9H-purin-9-yl)-1,3-dideoxy-3-(O-methyl-L-tyrosylamino)-β-D-ribofuranuronoyl]-β-phenyl-D,L-alanine (90 mg), mp. 192°-204° C. (dec.).

IR (nujol): 3650-2250, 1670, 1645, 1615, cm⁻¹.

NMR (DCl+D₂O, δ): 2.9-3.4 (4H, m), 3.84 (3H, s), 4.2-5.2 (5H, m), 6.10 (H, d, J=2 Hz), 6.90 (2H, d, J=8 Hz), 7.06 (5H, s), 7.25 (2H, d, J=8 Hz), 7.97 (1H, s), 8.33 (1H, s).

EXAMPLE 95

1-(6-Amino-9H-purin-9-yl)-1,3-dideoxy-3-[N-tert-butoxycarbonyl-O-(2,6-dichlorobenzyl)-L-tyrosylamino]-β-D-ribofuranuronic acid (260 mg) was prepared by reacting 1-(6-amino-9H-purin-9-yl)-1,3-dideoxy-3-amino-β-D-ribofuranuronic acid monohydrate (223.5 mg) prepared in Example 99 with N-hydroxysuccinimide ester of N-tert-butoxycarbonyl-O-(2,6-dichlorobenzyl)-L-tyrosine (388 mg) according to a similar manner to that of Example 5, mp. 166°-176° C. (dec.).

IR (nujol): 3650-2250, 1685, 1655, 1615 cm⁻¹.

NMR (DMSO-d₆+D₂O, δ): 1.40 (9H, s), 2.9 (2H, m), 4.0-5.0 (4H, m), 5.20 (2H, s), 6.20 (1H, bs), 6.93 (2H, d, J=8 Hz), 7.27 (2H, d, J=8 Hz), 7.5 (3H, m), 8.30 (1H, s), 8.57 (1H, s).

EXAMPLE 96

1-(6-Amino-9H-purin-9-yl)-1,3-dideoxy-3-[O-(2,6-dichlorobenzyl)-L-tyrosylamino]-β-D-ribofuranuronic acid (140 mg) was prepared from 1-(6amino-9H-purin-9-yl)-1,3-dideoxy-3-[N-tert-butoxycarbonyl-O-(2,6-dichlorobenzyl)-L-tyrosylamino]-β-D-ribofuranuronic acid (200 mg) prepared in Example 95 according to a similar manner to that of Example 89, mp. 180°-187° C. (dec.).

IR (nujol): 3650-2250, 1690, 1645, 1610 cm⁻¹.

NMR (DCl+D₂O, δ): 3.5 (2H, m), 4.2-5.4 (6H, m), 6.25 (1H, d, J=2 Hz), 7.0-7.4 (5H, m), 7.47 (2H, d, J=8 Hz), 8.63 (1H, s), 8.87 (1H, s).

EXAMPLE 97

An aqueous medium (100 ml) containing corn starch (2.0%), glucose (1.0%), corn steep liquor (1.0%), peanut meal (1%), dried yeast (0.5%) and calcium carbonate (0.5%) was poured into each of six flasks. The pH of the medium was adjusted to 6.0. The flasks were sealed by cotton wool and then sterilized at 120° C. for 20 minutes. A loopful of slant culture of *Chrysosporium pannorum* (Link) Hughes No. 4629 ATCC No. 20617 was inoculated to each of the flask and incubated on a reciprocal shaker for 96 hours at 25° C.

The resultant culture in three flasks was inoculated to an aqueous medium containing 2% of solublized starch (2%), glucose (1%), beat bone extract (3%) in each of two jar-fermenters which had been sterilized at 120° C. for 20 minutes in advance, and incubated at 28° C. for 160 hours. The cultured broth (total: 42 liters) thus obtained was filtered with an aid of diatomaceous earth (3 kg). The filtrate (32 liters; pH 7.2) was passed through a column containing 8 liters of polymeric adsorbent (Diaion HP-20) (trade mark, Mitsubishi Chemical Industries Ltd.). Monitering each fraction by a biological activity using a disc assay against *Candida albicans*, the column was washed with water and a 20% aqueous methanol solution (¼ of the broth volume) and then eluted with a 50% aqueous methanol solution (16 liters). The eluate was concentrated under reduced pressure to a volume of 2 liters. The concentrate was chromatographed on a CM Sephadex C-25 ($H^+$ type; Fine Chemical Co.) column (400 ml). The column was washed with water (400 ml) and then eluted with 0.1N aqueous hydrochloric acid (1.2 liters).

The active fractions were adjusted to pH 7.0 with 6N aqueous sodium hydroxide solution and passed through a column of polymeric adsorbent (Diaion HP-20, 300 ml). The column was washed with water and eluted with a 40% aqueous methanol solution. The eluate (600 ml) was concentrated to a volume of 400 ml and loaded on a column of DEAE-Sephadex A-25 in 1/10M phosphate buffer (200 ml) and eluted with deionized water (500 ml). Active fractions were desalted again on a column of polymeric adsorbent (Diaion HP-20, 100 ml). The eluate (400 ml) were concentrated to a volume of 50 ml. The concentrate was left to stand overnight in a refrigerator. The colorless needle crystals were collected by filtration and recrystallized from water to give colorless needle (135 mg) of 1-(6-amino-9H-purin-9-yl)-1,3-dideoxy-3-(O-methyl-L-tyrosylamino)-β-D-ribofuranuronic acid monohydrate, mp. 228°–232° C. (dec.).

Elementary analysis: Calculated for $C_{20}H_{23}N_7O_6 \cdot H_2O$: C 50.52; H 5.30; N 20.62 (%). Found: C 50.62; H 4.98; N 21.02 (%).

EXAMPLE 98

The cultured broth (45 liters) prepared in a similar manner to Example 97 was filtered with a filter aid (Radiolite #600, Showa Kagaku Co.). The filtrate (pH 7.0) was passed through a column of polymeric adsorbent (Diaion HP-20, 8 liters). The column was washed with water and a 20% aqueous methanol solution. The column was then eluted with a 50% aqueous methanol solution (16 liters). The eluate was concentrated to a volume of 5 liters. The concentrate was chromatographed on a CM-Sephadex C-25 ($H^+$ form) column (1 liter). The column was washed with deionized water (1 liter) and then eluted with a 0.1N aqueous hydrochloric acid solution (2 liters). The eluate was concentrated to a volume of 500 ml. The pH of the concentrate was adjusted to pH 7.0 with a 6N aqueous sodium hydroxide solution. The solution was kept overnight in a refrigerator. The crude crystals (1.85 g) were collected by filtration. The crystal was dissolved in 90 ml of a 0.05N aqueous hydrochloric acid solution. The solution was treated with 180 mg of activated carbon. After the carbon was filtered off, the filtrate was left to stand overnight in a refrigerator. Colorless crystals were separated, collected and washed with water to give 1-(6-amino-9H-purin-9-yl)-1,3-dideoxy-3-(O-methyl-L-tyrosylamino)-β-D-ribofuranuronic acid hydrochloride dihydrate (1.1 g), mp. 198°–220° C. (dec.).

Elementary analysis: Calculated for $C_{20}H_{23}N_7O_6 \cdot HCl \cdot 2H_2O$: C 45.33; H 5.33; N 18.50; Cl 6.69 (%). Found: C 45.14; H 5.01; N 18.67; Cl 7.04.

1-(6-Amino-9H-purin-9-yl)-1,3-dideoxy-3-(O-methyl-L-tyrosylamino)-β-D-ribofuranuronic acid dihydrochloride monohydrate (177 mg) was obtained from the mother liquor, mp. 215°–233° C. (dec.).

Elementary analysis: Calculated for $C_{20}H_{23}N_7O_6 \cdot 2HCl \cdot H_2O$: C 43.80; H 4.96; N 17.88; Cl 12.93 (%). Found: C 43.49; H 4.82; N 18.25; Cl 13.04 (%).

EXAMPLE 99

A mixture of 1-(6-amino-9H-purin-9-yl)-1,3-dideoxy-3-(O-methyl-L-tyrosylamino)-β-D-ribofuranuronic acid dihydrochloride monohydrate (5.48 g) prepared in Example 98 in 1N methanolic sodium hydroxide solution (1000 ml) was heated under reflux for 20 hours. The reaction mixture was evaporated and the residue was neutralized with concentrated hydrochloric acid. The aqueous solution was subjected to column chromatography on a non-ionic adsorption resin "HP-20" (trade mark, Mitsubishi Chemical Industries Ltd.) (500 ml). The elution was carried out with water, and the eluate was concentrated, stood overnight. The resulting precipitates were collected, washed with water, and dried to give 1-(6-amino-9H-purin-9-yl)-1,3-dideoxy-3-amino-β-D-ribofuranuronic acid monohydrate (2.47 g).

IR (nujol): 3480, 3600–2100 (broad), 1655, 1600, 1575 $cm^{-1}$.

NMR ($D_2O+DCl$, δ): 8.43 (1H, s), 8.34 (1H, s), 6.33 (1H, d, J=2 Hz), 5.13 (1H, dd, J=2 Hz, 6 Hz).

FD Mass: 281 (M+1) $[α]_D^{20}$: −28° (C=0.25, 1N-HCl).

Elementary Analysis: Calculated for $C_{10}H_{12}N_6O_4 \cdot H_2O$: C 40.27; H 4.73; N 28.18 (%). Found: C 39.98, H 4.62; N 28.21 (%).

What is claimed is:

1. A compound of the formula:

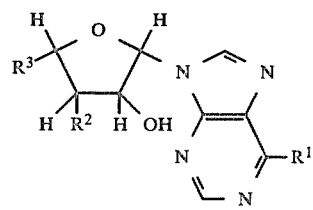

wherein
$R^1$ is amino or a protected amino group,
$R^2$ is amino or acylamino and
$R^3$ is carboxy or a protected carboxy group
or a pharmaceutically acceptable salt thereof.

2. A compound of claim 1, which is ribofuranuronic acid derivative of the formula:

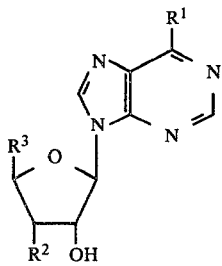

wherein $R^1$, $R^2$ and $R^3$ are each as defined above.

3. A compound of claim 2, wherein
$R^1$ is amino or an acylamino group,
$R^2$ is amino or an acylamino group and
$R^3$ is carboxy, an esterified carboxy group or an amidated carboxy group.

4. A compound of claim 3, wherein
$R^2$ is amino.

5. A compound of claim 4, which is 1-(6-amino-9H-purin-9-yl)-1,3-dideoxy-3-amino-β-D-ribofuranuronic acid.

6. A compound of claim 3, wherein
$R^2$ is acylamino.

7. A compound of claim 6, wherein
$R^1$ is amino or benzoylamino;
$R^2$ is lower alkanoylamino which may have one or more suitable substituent(s) selected from the groups consisting of amino, lower alkoxycarbonylamino, phenyl(lower)alkoxycarbonylamino, carboxy, lower alkoxycarbonyl, phenyl(lower)alkoxycarbonyl, guanidino, and bis[phenyl(lower)alkoxycarbonyl]guanidino; benzoylamino; phenyl(lower)alkanoylamino which may have one or more suitable substituent(s) selected from the groups consisting of hydroxy, amino, lower alkoxycarbonylamino, phenyl(lower) alkoxycarbonylamino, phenyl(lower)alkoxy, dihalophenyl(lower)alkoxy, lower alkoxy, halogen, nitro, amino(lower)alkoxy, lower alkoxycarbonylamino(lower)alkoxy, carbazoylamino, lower alkylcarbamoylamino, carboxy(lower)alkoxy, lower alkoxycarbonyl(lower)alkoxy, lower alkanoylamino, nitrophenyl(lower)alkoxycarbonyl, amino(lower)alkanoylamino, phenyl(lower)alkoxycarbonylamino(lower)alkanoylamino, phenyl(lower)alkanoylamino having amino, phenyl(lower)alkanoylamino having lower alkoxycarbonylamino, lower alkoxyphenyl(lower)alkanoylamino having amino, lower alkoxyphenyl(lower)alkanoylamino having lower alkoxycarbonylamino, guanidino(lower)alkanoylamino having amino, and bis[phenyl(lower)alkoxycarbonyl]guanidino(lower)alkanoylamino having phenyl(lower)alkoxycarbonylamino; or phenyl(lower)alkenoylamino; and
$R^3$ is carboxy, succinimidoxycarbonyl, lower alkoxycarbonyl, lower alkylcarbamoyl, carboxy(lower)alkylcarbamoyl, carbazoyl, phenyl(lower)alkylcarbamoyl having carboxy, or phenyl(lower)alkylcarbamoyl having phenyl(lower)alkoxycarbonyl.

8. A compound of claim 7, wherein
$R^1$ is amino or benzoylamino;
$R^2$ is alanylamino, β-alanylamino, N-benzyloxycarbonylalanylamino, N-benzyloxycarbonyl-β-alanylamino, lysylamino, $N^\alpha,N^\epsilon$-dibenzyloxycarbonyllysylamino, α-glutamylamino, 2-amino-4-benzyloxycarbonylbutyrylamino, 2-tert-butoxycarbonylamino-4-benzyloxycarbonylbutyrylamino, arginylamino, tribenzyloxycarbonylarginylamino, benzoylamino, phenylacetylamino, 3-phenylpropionylamino, mandelylamino, phenylglycylamino, phenylalanylamino, 3-amino-3phenylpropionylamino, N-tert-butoxycarbonylphenylglycylamino, N-benzyloxycarbonylphenylalanylamino, 3-tert-butoxycarbonylamino-3-phenylpropionylamino, β-(4-aminophenyl)alanylamino, N-tert-butoxycarbonyl-β-(4-tert-butoxycarbonylaminophenyl)alanylamino, β-phenylserylamino, tyrosylamino, N-benzyloxycarbonyl-β-phenylserylamino, N-benzyloxycarbonyl-O-benzyltyrosylamino, O-(2,6-dichlorobenzyl)-L-tyrosylamino, N-tert-butoxycarbonyl-O-(2,6-dichlorobenzyl)tyrosylamino, O-methyl-β-phenylserylamino, O-methyltyrosylamino, N-tert-butoxycarbonyl-O-methyl-β-phenylserylamino, N-benzyloxycarbonyl-O-methyltyrosylamino, N-tert-butoxycarbonyl-O-methyltyrosylamino, β-(2chlorophenyl)alanylamino, β-(3-chlorophenyl)alanylamino, β-(4-chlorophenyl)alanylamino, β-(4fluorophenyl)alanylamino, N-tert-butoxycarbonyl-β-(2-chlorophenyl)alanylamino, N-tert-butoxycarbonyl-β-(3-chlorophenyl)alanylamino, N-tert-butoxycarbonyl-β-(4-chlorophenyl)alanylamino, N-tert-butoxycarbonyl-β-(4fluorophenyl)alanylamino, β-(4-nitrophenyl)alanylamino, N-tert-butoxycarbonyl-β-(4-nitrophenyl)alanylamino, O-(3-aminopropyl)-tyrosylamino, N-tert-butoxycarbonyl-O-(3tert-butoxycarbonylaminopropyl)tyrosylamino, N-carbazoyl-O-methyltyrosylamino, N-butylcarbamoyl-O-methyltyrosylamino, O-carboxymethyltyrosylamino, N-tert-butoxycarbonyl-O-methoxycarbonylmethyltyrosylamino, N-formylphenylalanylamino, 2-(4-nitrobenzyloxycarbonyl)-2phenylacetylamino, N-glycyl-O-methyltyrosylamino, N-(N-benzyloxycarbonylglycyl)-O-methyltyrosylamino, N-(β-phenylalanyl)-O-methyltyrosylamino, N-(N-tert-butoxycarbonyl-β-phenylalanyl)-O-methyltyrosylamino, N-(O-methyltyrosyl)-O-methyltyrosylamino, N-(N-tert-butoxycarbonyl-O-methyltyrosyl)-O-methyltyrosylamino, N-arginyl-O-methyltyrosylamino, N-(tribenzyloxycarbonylarginyl)-O-methyltyrosylamino or cinnamoylamino;
$R^3$ is carboxy, succinimidoxycarbonyl, methoxycarbonyl, ethoxycarbonyl, butylcarbamoyl, carboxymethylcarbamoyl, carbazoyl, 1-carboxy-2phenylcarbamoyl or 1-benzyloxycarbonyl-2-phenylethylcarbamoyl.

9. A compound of claim 8, which is 1-(6-amino-9H-purin-9-yl)-1,3-dideoxy-3-(O-methyl-L-tyrosylamino)-β-D-ribofuranuronic acid or its mono(or di)hydrate or mono(or di)hydrochloride thereof.

10. A compound of claim 9 which is 1-(6-amino-9H-purin-9-yl)-1,3-dideoxy-3-(O-methyl-L-tyrosylamino)-β-D-ribofuranuronic acid mono hydrate dihydrochloride.

11. An antimicrobial pharmaceutical composition comprising an antimicrobially effective amount of a compound of claim 1 or a pharmaceutically acceptable salt thereof in association with a pharmaceutically acceptable, substantially non-toxic carrier or excipient.

* * * * *